United States Patent
Kimmel et al.

(10) Patent No.: US 9,821,143 B2
(45) Date of Patent: Nov. 21, 2017

(54) STEERABLE SHEATH INCLUDING ELASTOMERIC MEMBER

(71) Applicant: IMRICOR MEDICAL SYSTEMS, INC., Burnsville, MN (US)

(72) Inventors: Scott Kimmel, Roseville, MN (US); Douglas A. Page, Apple Valley, MN (US)

(73) Assignee: IMRICOR MEDICAL SYSTEMS, INC., Burnsville, MN (US)

(*) Notice: Subject to any disclaimer, the term of this patent is extended or adjusted under 35 U.S.C. 154(b) by 49 days.

(21) Appl. No.: 14/867,487

(22) Filed: Sep. 28, 2015

(65) Prior Publication Data

US 2016/0058974 A1 Mar. 3, 2016

Related U.S. Application Data

(63) Continuation of application No. PCT/US2015/051910, filed on Sep. 24, 2015, and a
(Continued)

(51) Int. Cl.
*A61M 25/01* (2006.01)
*A61B 5/055* (2006.01)
(Continued)

(52) U.S. Cl.
CPC .... *A61M 25/0127* (2013.01); *A61M 25/0136* (2013.01); *A61M 25/0147* (2013.01);
(Continued)

(58) Field of Classification Search
CPC .......... A61M 25/0127; A61M 25/0136; A61M 25/0147; A61M 25/0052; A61M 25/0054; A61M 25/0108; G01R 33/286
(Continued)

(56) References Cited

U.S. PATENT DOCUMENTS 5,364,351 A * 11/1994 Heinzelman ...... A61M 25/0147
600/585
5,507,725 A 4/1996 Savage et al.
(Continued)

FOREIGN PATENT DOCUMENTS

DE 69333140 T2 6/2004
DE 102011121964 A1 6/2013
(Continued)

OTHER PUBLICATIONS

International Search Report and Written Opinion issued by the ISA/U.S., regarding international patent application Serial No. PCT/US2015/051910, dated Dec. 18, 2015, 10 pages; USA.
(Continued)

*Primary Examiner* — Gary Jackson
*Assistant Examiner* — Zahed Kabir
(74) *Attorney, Agent, or Firm* — Fox Rothschild LLP

(57) ABSTRACT

An MR compatible steerable sheath with elastomeric member is provided. The elastomeric member is configured to serve as a reservoir and receive contrast media therewithin. The elastomeric member is positioned on the distal end of the steerable sheath and may circumferentially surround the sheath shaft or be offset from a longitudinal axis thereof. In operation, the contrast media allows a user to view the distal tip of the steerable sheath by virtue of the contrast media contained within the elastomeric member.

16 Claims, 29 Drawing Sheets

Related U.S. Application Data continuation-in-part of application No. 14/705,617, filed on May 6, 2015, now Pat. No. 9,192,743, which is a continuation of application No. 14/106,177, filed on Dec. 13, 2013, now Pat. No. 9,138,561, which is a continuation-in-part of application No. 13/819,981, filed as application No. PCT/US2012/069487 on Dec. 13, 2012, now abandoned, said application No. 14/106,177 is a continuation of application No. PCT/US2013/074331, filed on Dec. 11, 2013.

(60) Provisional application No. 62/054,723, filed on Sep. 24, 2014, provisional application No. 61/576,161, filed on Dec. 15, 2011.

(51) Int. Cl.
*G01R 33/28* (2006.01)
*A61M 25/00* (2006.01)

(52) U.S. Cl.
CPC ..... *A61M 25/0052* (2013.01); *A61M 25/0054* (2013.01); *A61M 25/0108* (2013.01); *G01R 33/286* (2013.01)

(58) Field of Classification Search
USPC .......................................................... 606/1
See application file for complete search history.

(56) References Cited

U.S. PATENT DOCUMENTS

| | | | |
|---|---|---|---|
| 5,531,664 A | 7/1996 | Adachi et al. | |
| 5,545,200 A | 8/1996 | West et al. | |
| 5,603,697 A | 2/1997 | Grundy et al. | |
| 5,656,029 A | 8/1997 | Imran et al. | |
| 5,715,817 A | 2/1998 | Stevens-Wright et al. | |
| 5,735,795 A | 4/1998 | Young et al. | |
| 5,759,173 A | 6/1998 | Preissman et al. | |
| 5,826,576 A | 10/1998 | West | |
| 5,897,529 A | 4/1999 | Ponzi | |
| 5,906,590 A | 5/1999 | Hunjan et al. | |
| 5,938,616 A | 8/1999 | Eaton et al. | |
| 6,022,319 A | 2/2000 | Williard et al. | |
| 6,030,360 A | 2/2000 | Biggs | |
| 6,123,699 A | 9/2000 | Webster, Jr. | |
| 6,126,654 A | 10/2000 | Giba et al. | |
| 6,183,435 B1 | 2/2001 | Bumbalough et al. | |
| 6,251,092 B1 | 6/2001 | Qin et al. | |
| 6,261,255 B1 | 7/2001 | Mullis et al. | |
| 6,267,746 B1 | 7/2001 | Bumbalough | |
| 6,458,088 B1 | 10/2002 | Hurtak et al. | |
| 6,468,260 B1 * | 10/2002 | Bumbalough | A61M 25/0136 600/434 |
| 6,485,455 B1 | 11/2002 | Thompson et al. | |
| 6,551,271 B2 | 4/2003 | Nguyen | |
| 6,579,278 B1 | 6/2003 | Bencini | |
| 6,582,536 B2 | 6/2003 | Shimada | |
| 6,589,226 B1 | 7/2003 | Owens | |
| 6,611,720 B2 | 8/2003 | Hata et al. | |
| 6,620,150 B2 | 9/2003 | Klemenelj | |
| 6,858,024 B1 | 2/2005 | Berg et al. | |
| 6,945,956 B2 | 9/2005 | Waldhauser et al. | |
| 6,976,987 B2 | 12/2005 | Flores | |
| 7,048,711 B2 | 5/2006 | Rosenman et al. | |
| 7,056,314 B1 | 6/2006 | Florio et al. | |
| 7,171,275 B2 | 1/2007 | Hata et al. | |
| 7,344,515 B2 | 3/2008 | Coyle | |
| 7,377,906 B2 | 5/2008 | Seikee | |
| 7,402,151 B2 | 7/2008 | Rosenman et al. | |
| 7,465,288 B2 | 12/2008 | Dudney et al. | |
| 7,591,784 B2 | 9/2009 | Butler | |
| 7,596,402 B2 | 9/2009 | Duerk et al. | |
| 7,606,609 B2 | 10/2009 | Muranushi et al. | |
| 7,615,044 B2 | 11/2009 | Scheibe et al. | |
| 7,682,319 B2 | 3/2010 | Martin et al. | |
| 7,682,358 B2 | 3/2010 | Gullickson et al. | |
| 7,691,095 B2 | 4/2010 | Bednarek et al. | |
| 7,803,130 B2 | 9/2010 | Ryan et al. | |
| 7,850,811 B2 | 12/2010 | Hart et al. | |
| 7,912,531 B1 | 3/2011 | Chiu et al. | |
| 7,955,305 B2 | 6/2011 | Moberg et al. | |
| 7,972,323 B1 | 7/2011 | Bendni et al. | |
| 8,016,784 B1 | 9/2011 | Hayzeiden et al. | |
| 8,043,288 B2 | 10/2011 | Dando et al. | |
| 8,075,476 B2 | 12/2011 | Vargas | |
| 8,096,985 B2 | 1/2012 | Legaspi et al. | |
| 8,137,308 B2 | 3/2012 | Schultz | |
| 8,226,641 B2 | 7/2012 | Potter | |
| 8,260,399 B2 | 9/2012 | Karmarkar et al. | |
| 8,308,659 B2 | 11/2012 | Scheibe et al. | |
| 8,376,990 B2 | 2/2013 | Ponzi et al. | |
| 8,473,029 B2 | 6/2013 | Gerhart et al. | |
| 2001/0032007 A1 | 10/2001 | Hata et al. | |
| 2005/0070844 A1 | 3/2005 | Chow et al. | |
| 2006/0100640 A1 * | 5/2006 | Bolduc | A61B 17/00234 606/108 |
| 2006/0229700 A1 * | 10/2006 | Acosta | A61F 2/915 623/1.11 |
| 2006/0264894 A1 | 11/2006 | Moberg et al. | |
| 2007/0073098 A1 | 3/2007 | Lenker et al. | |
| 2008/0161790 A1 * | 7/2008 | Dando | A61B 18/1492 606/41 |
| 2008/0161843 A1 | 7/2008 | Clague | |
| 2008/0300571 A1 * | 12/2008 | LePivert | A61B 18/1492 604/503 |
| 2009/0163915 A1 | 6/2009 | Potter | |
| 2009/0171272 A1 | 7/2009 | Tegg et al. | |
| 2009/0281524 A1 * | 11/2009 | Scheibe | A61M 25/0136 604/528 |
| 2009/0287187 A1 | 11/2009 | Legaspi et al. | |
| 2009/0312698 A1 * | 12/2009 | Farrell | A61M 25/0009 604/95.04 |
| 2010/0076408 A1 | 3/2010 | Krever et al. | |
| 2010/0168827 A1 | 7/2010 | Schultz | |
| 2010/0198049 A1 | 8/2010 | Karmarkar et al. | |
| 2010/0217261 A1 | 8/2010 | Watson | |
| 2011/0087270 A1 | 4/2011 | Penner | |
| 2011/0264074 A1 | 10/2011 | Tegg et al. | |
| 2011/0264133 A1 | 10/2011 | Hanlon et al. | |
| 2011/0282176 A1 | 11/2011 | Tegg | |
| 2012/0010490 A1 | 1/2012 | Kauphusman et al. | |
| 2012/0017923 A1 | 1/2012 | Sobe | |
| 2012/0089125 A1 | 4/2012 | Scheibe et al. | |
| 2012/0123327 A1 | 5/2012 | Miller | |
| 2012/0130218 A1 | 5/2012 | Kauphusman et al. | |
| 2012/0172717 A1 | 7/2012 | Gonda | |
| 2012/0190927 A1 | 7/2012 | Ulhlein | |
| 2012/0226228 A1 | 9/2012 | Butler | |
| 2012/0277582 A1 * | 11/2012 | Mafi | A61B 5/6858 600/431 |
| 2012/0310212 A1 | 12/2012 | Fischell et al. | |
| 2013/0018306 A1 | 1/2013 | Ludwin | |
| 2013/0116705 A1 | 5/2013 | Salahieh et al. | |
| 2013/0165857 A1 | 6/2013 | O'Donnell et al. | |
| 2013/0165922 A1 | 6/2013 | Faiwell et al. | |
| 2013/0184642 A1 | 7/2013 | O'Donnell et al. | |
| 2013/0317542 A1 | 11/2013 | Clark et al. | |
| 2014/0018732 A1 * | 1/2014 | Bagaoisan | A61M 25/0147 604/95.04 |
| 2014/0100445 A1 | 4/2014 | Stenzel et al. | |

FOREIGN PATENT DOCUMENTS

| | | |
|---|---|---|
| EP | 0713408 A1 | 5/1996 |
| EP | 1676596 A1 | 5/2006 |
| EP | 1803481 A2 | 4/2007 |
| EP | 2116272 A1 | 11/2009 |
| WO | WO-0117600 A1 | 3/2001 |
| WO | WO 2007-046953 A2 | 4/2007 |
| WO | WO 2010-082150 A1 | 7/2010 |
| WO | WO 2011-051872 A2 | 5/2011 |
| WO | WO 2011-055143 A1 | 5/2011 |

(56) References Cited

FOREIGN PATENT DOCUMENTS

| WO | WO-2012019232 A1 | 2/2012 |
|----|------------------|--------|
| WO | WO 2012-158263 A1 | 11/2012 |
| WO | 2013057609 A1 | 4/2013 |
| WO | 2013134708 A1 | 9/2013 |

OTHER PUBLICATIONS

International Search Report and Written Opinion issued by the ISA/U.S., regarding international patent application Serial No. PCT/US2015/050585, dated Dec. 14, 2015, 7 pages; USA.
International Search Report and Written Opinion issued by the ISA/U.S., regarding international patent application Serial No. PCT/US2015/050588, dated Dec. 17, 2015, 9 pages; USA.
Chinese Patent First Office Action issued by the State Intellectual Property Office of P.R. China, regarding corresponding patent application Serial No. 201380065624.5, dated Jun. 3, 2016, 13 pages; P.R. China—translated.
International Search Report and Written Opinion issued by the ISA/U.S. Receiving Office, regarding corresponding patent application Serial No. PCT/US2013/074331; dated Feb. 20, 2014; 15 pages.
International Search Report and Written Opinion issued by the ISA/U.S. Receiving Office, regarding corresponding patent application Serial No. PCT/US2012/069487; dated Feb. 26, 2013; 13 pages.
Supplemental European Search Report and Opinion, issued by the European Patent Office, regarding corresponding patent application Serial No. EP 13862105.7; dated Nov. 18, 2016; 8 pages. EPO.
Canadian Office Action issued by the Canadian Intellectual Property Office, in regard to corresponding patent application Serial No. 2894763; dated Apr. 22, 2016; 4 pages.

* cited by examiner

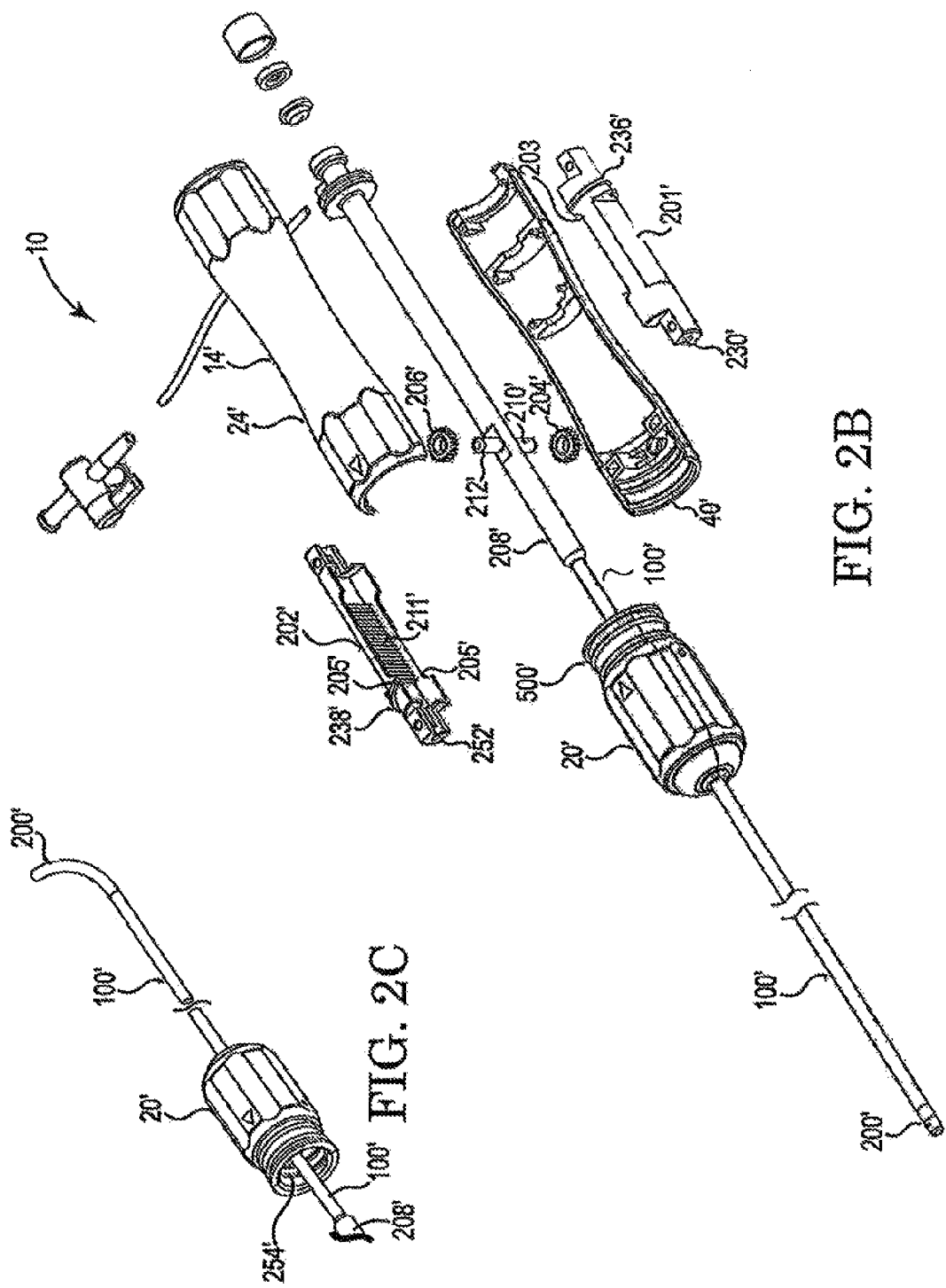

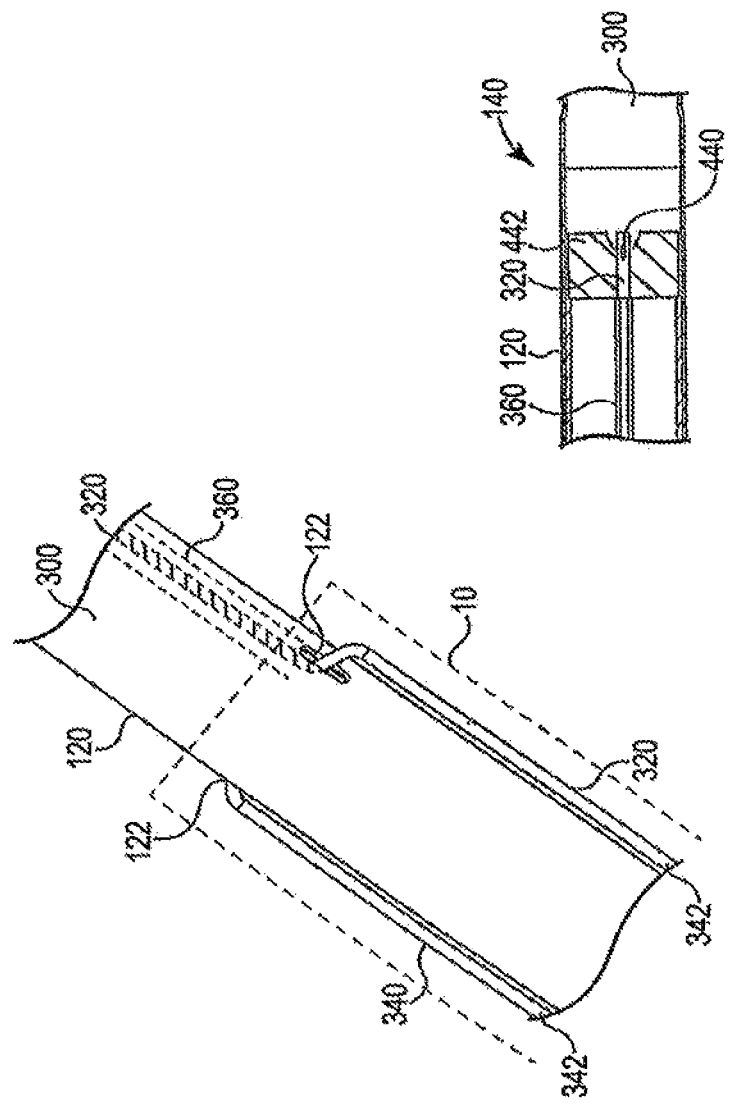

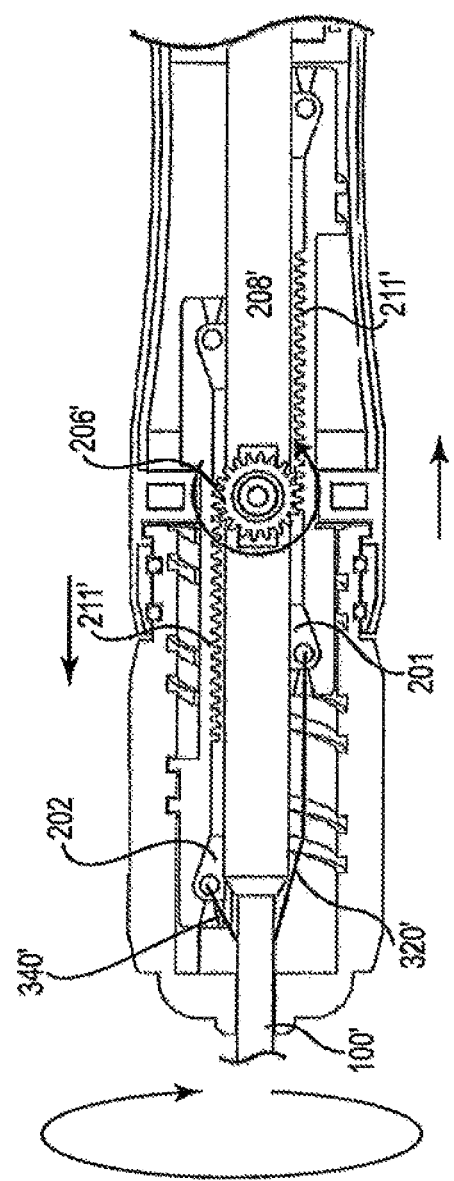

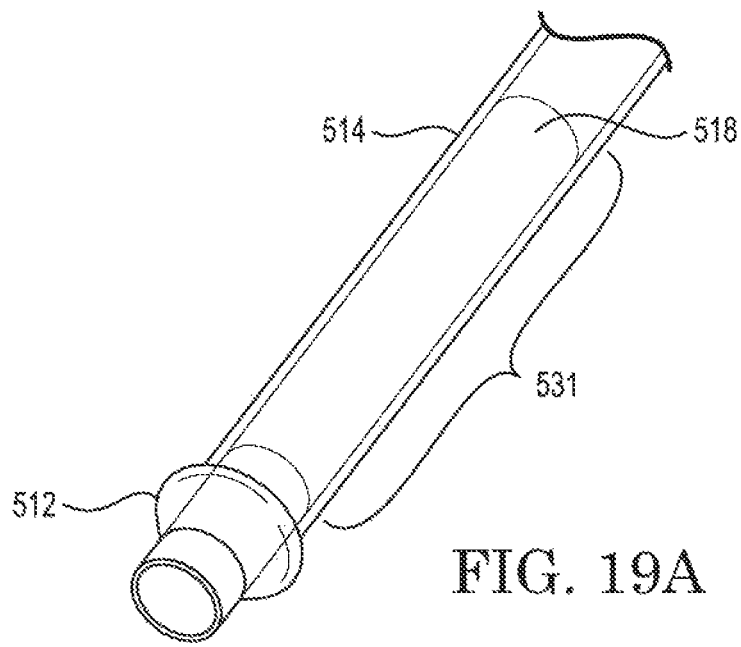
FIG. 19A
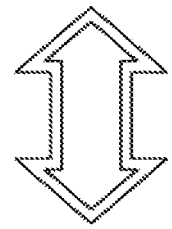
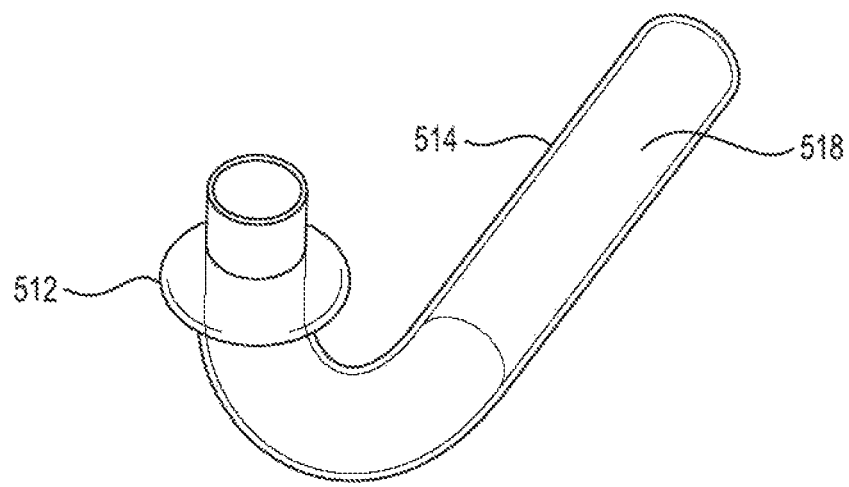
FIG. 19B

STEERABLE SHEATH INCLUDING ELASTOMERIC MEMBER

CROSS REFERENCE TO RELATED APPLICATIONS

This application is a continuation of PCT patent application Serial No.: PCT/US2015/051910, filed on Sep. 24, 2015; which claims the benefit of priority to U.S. Provisional patent application Ser. No. 62/054,723, filed on Sep. 24, 2014; and this application is also a continuation-in-part of U.S. patent application Ser. No. 14/705,617, filed on May 6, 2015; which is a continuation of U.S. application Ser. No. 14/106,177, filed on Dec. 13, 2013, now U.S. Pat. No. 9,138,561, issued Sep. 22, 2015; which is a continuation-in-part of U.S. application Ser. No. 13/819,981, filed on (§371 date) Jan. 20, 2014, (abandoned); which claims the benefit of PCT application Serial No.: PCT/US2012/069487, filed on Dec. 13, 2012; which claims the benefit of U.S. Provisional application Ser. No. 61/576,161, filed on Dec. 15, 2011; and U.S. application Ser. No. 14/106,177 is a continuation application of PCT application Serial No.: PCT/US2013/074331, filed on Dec. 11, 2013. The entireties of all of the foregoing are hereby incorporated by reference.

FIELD OF THE INVENTION

This invention relates to deflectable medical catheters, namely steerable sheaths used in interventional vascular procedures to deliver tools into the human body. More particularly, the present invention is related to a steerable sheath having an elastomeric member bonded to an outer portion thereof and configured to receive contrast media therewithin.

BACKGROUND OF THE INVENTION

Deflectable medical catheters, namely steerable sheaths, are used in interventional vascular procedures to deliver tools (e.g. electrophysiology catheters, guidewires, elastomeric members catheters, stents, instruments, etc.) into the human body. More particularly, the present invention is related to a family of sheaths that incorporate one or more elastomeric members that serve as a reservoir for a contrast agent. The deflectable elastomeric member sheath is safe for use in the magnetic resonance environment and the elastomeric member and deflectable sheath tip is rendered visible by the contrast agent.

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

A variety of MRI techniques are being developed as alternatives to X-ray imaging for guiding interventional procedures. For example, as a medical device is advanced through the patient's body during an interventional procedure, its progress may be tracked so that the device can be delivered properly to a target site. Once delivered to the target site, the device and patient tissue may be monitored to improve therapy delivery. Thus, tracking the position of medical devices is useful in interventional procedures. Exemplary interventional procedures include, for example, cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like. Tracking the position of medical devices using MRI is also useful in oncological procedures such as breast, liver and prostate tumor ablations; and urological procedures such as uterine fibroid and enlarged prostate ablations.

MRI uses three fields to image patient anatomy: a large static magnetic field, a time-varying magnetic gradient field, and a radiofrequency (RF) electromagnetic field. The static magnetic field and time-varying magnetic gradient field work in concert to establish both proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

Each of the three fields associated with MRI presents safety risks to patients when a medical device is in close proximity to or in contact either externally or internally with patient tissue. One important safety risk is the heating that may result from an interaction between the RF field of the MRI scanner and the medical device (RF-induced heating), especially medical devices that have elongated conductive structures, such as braiding and pull-wires in catheters and sheaths.

The RF-induced heating safety risk associated with elongated metallic structures in the MRI environment results from a coupling between the RF field and the metallic structure. In this case several heating related conditions exist. One condition exists because the metallic structure electrically contacts tissue. RF currents induced in the metallic structure may be delivered into the tissue, resulting in a high current density in the tissue and associated Joule or Ohmic tissue heating. Also, RF induced currents in the metallic structure may result in increased local specific absorption of RF energy in nearby tissue, thus increasing the tissue's temperature. The foregoing phenomenon is referred to as dielectric heating. Dielectric heating may occur even if the metallic structure does not electrically contact tissue, such metallic braiding used in a steerable sheath. In addition, RF induced currents in the metallic structure may cause Ohmic heating in the structure, itself, and the resultant heat may transfer to the patient. In such cases, it is important to attempt to both reduce the RF induced current present in the metallic structure and/or eliminate it all together by eliminating the use of metal braid and long metallic pull-wires.

The static field of the MRI will cause magnetically induced displacement torque on any device containing ferromagnetic materials and has the potential to cause unwanted device movement. It is important to construct the sheath and control handle from non-magnetic materials, to eliminate the risk of unwanted device movement.

When performing interventional procedures under MRI guidance, clinical grade image quality must be maintained. Conventional steerable sheaths are not designed for the MRI and may cause image artifacts and/or distortion that significantly reduce image quality. Constructing the sheath from non-magnetic materials and eliminating all potentially resonant conductive structures allows the sheath to be used during active MR imaging without impacting image quality. Similarly, it is as important to ensure that the control handle is also constructed from non-magnetic materials thereby eliminating potentially resonant conductive structures that may prevent the control handle being used during active MR imaging.

Importantly, there is a need for an improved steerable sheath that incorporates one or more elastomeric members to create a reservoir for the injection of an MRI contrast agent. When the contrast agent is injected into the elastomeric member, the elastomeric member expands and becomes visible on the image generated during the MRI scan. During this process, the sheath, otherwise invisible on the MRI scan, is rendered visible at the location of the contrast filled elastomeric member resulting in better visualization and tracking of the sheath tip.

BRIEF SUMMARY OF THE INVENTION

The foregoing need is addressed by the steerable elastomeric member sheath with the invention. Those of skill in the art will appreciate that the steerable elastomeric member sheath in accordance with the invention is disclosed as being utilized with the steerable sheath and control handle as described herein but may also be utilized with other steerable sheaths and control handles, all of which fall within the scope of the invention.

In one aspect of the invention a steerable sheath is provided that may be used in an MRI environment to deliver a variety of tools (catheters, guidewires, implantable devices, etc.) into the lumens of the body.

In a further aspect of the invention, the steerable sheath shaft comprises a reinforced polymer tube in which the reinforcing material is non-metallic based (Kevlar, PEEK, Nylon, fabric, polyimide, etc.) or a hybrid of metallic and non-metallic materials and the reinforcing geometry may comprise a braid, a coil, or a slit tube that mimics a coil and combinations of the foregoing. In yet another aspect of the invention, the reinforced polymer tube may also be segmented with varying flexibility along its length to provide the user with the ability to deflect the catheter in a region in which the segment is more flexible than other segments.

In yet another aspect of the invention the polymer tube may also include one or more passive visualization markers along the length of the tube and/or one or more active visualization markers along the length of the tube.

The steerable sheath in accordance with the invention also includes one or more pull-wires which are coupled with the reinforced tube and that allow the user to manipulate and deflect the polymer tube. In one aspect of the invention, the pull-wires are preferably made of a non-metallic material (Kevlar, PEEK, Nylon, fabric, etc.). One or more internal pull-wire lumens are positioned within the polymer tube construct and allow the user to manipulate the pull-wires to move smoothly during actuation. One or more anchor points connect the pull-wire in the distal portion of the polymer tube.

In another aspect of the invention a control handle on the proximal end of the reinforced tube operates longitudinal movement of the pull-wire(s). In one aspect of the invention, the handle includes paramagnetic or diamagnetic materials or combinations of paramagnetic and diamagnetic materials.

In another aspect of the invention, an elastomeric member may circumferentially encompass the outer diameter of the sheath shaft or may be bonded to an outer portion thereof.

In another aspect of the invention, a deflectable sheath may integrally or non-integrally incorporate the elastomeric member.

In another aspect of the invention, the elastomeric member may be designed to be of a variety of shapes such as circular, conical, square, spherical, elliptical, tapered, dog bone, paddle, offset and/or toridal.

In another aspect of the invention, the sheath may include a single tube lumen or a multiple tube lumen that is fluidly coupled with the elastomeric member.

In another aspect of the invention, the deflectable sheath may incorporate one, two, three four offset-shaped elastomeric members.

In another aspect of the invention, the lumen(s) used to fill the elastomeric member(s) have a diameter sufficient to allow for the injection of viscous fluids into the elastomeric member and allow for quick inflation and deflation of the elastomeric member.

In another aspect of the invention, the lumen(s) used to fill the elastomeric member are coated to minimize resistance between the lumen wall and liquid within the lumen and allow for quick inflation and deflation of the elastomeric member.

In another aspect of the invention, the elastomeric member is made sufficiently pliable to allow it to inflate with viscous fluid without requiring excessive pressure at the injection site or within the lumen used to fill the elastomeric member.

In another aspect of the invention the elastomeric member comprises an inflatable balloon.

In another aspect of the invention, an MR compatible steerable sheath is provided. The MR compatible steerable sheath includes a steerable shaft including a proximal end and a deflectable distal tip, the steerable shaft configured to receive first and second longitudinal movement wires operably coupled to the deflectable distal tip; an elastomeric member operably coupled to the proximal end of the steerable shaft and configured to receive contrast media; a control handle having a main body configured to receive first and second rack screws, the second rack screw including a threaded portion on an outer surface thereof, the steerable shaft extending axially through the control handle; the first longitudinal movement wire operably coupled to the first rack screw and the second longitudinal movement operably coupled to the second rack screw; and a rotatable adjustment knob operably engageable with the control handle, the rotatable adjustment knob having an internal threaded portion matingly engageable with the threaded portion of the second rack screw, the rotatable adjustment knob moveable between a first position in which the internal thread is configured to engage the thread on the outer surface of the second rack screw and cause the second rack screw to move proximally to cause proximal longitudinal movement of the second longitudinal movement wire and a second position in which the internal thread is configured to move the second rack screw in a distal direction to release tension on the second longitudinal movement wire, wherein the elastomeric member is configured to receive contrast media therewithin causing the elastomeric member to expand and becomes visible on an image generated during an MRI scan.

While multiple embodiments, objects, features and advantages are disclosed, still other embodiments of the invention will become apparent to those of ordinary skill in the art from the following detailed description taken together with the accompanying figures, the foregoing being illustrative and not restrictive.

BRIEF DESCRIPTION OF THE DRAWINGS

For a better understanding of the invention, and to show how the same may be carried into effect, reference will now be made, by way of example, to the accompanying drawings, in which:

FIG. 2B is an exploded perspective view of the control handle and steerable sheath according to another aspect of the invention.

FIG. 2C is an enlarged view of the rotatable adjustment knob including internal threads that are circumferentially disposed about an inner wall thereof.

FIG. 5A is an enlarged view of the pull wires at the proximal end of the steerable sheath shaft in accordance with the invention.

FIG. 5B is a detailed view of a pull ring that provides a contact point between the pull wire and the distal end of the steerable sheath shaft in one aspect of the invention.

FIG. 8B is an enlarged view of the control handle mechanical structure denoted by 800' in FIG. 6B and showing counterclockwise rotation of rotatable knob.

FIGS. 19A and 19B are perspective views depicting the deflection region of the catheter sheath and the location of the elastomeric member distal to the deflection region.

DETAILED DESCRIPTION OF THE INVENTION

Figure 1:
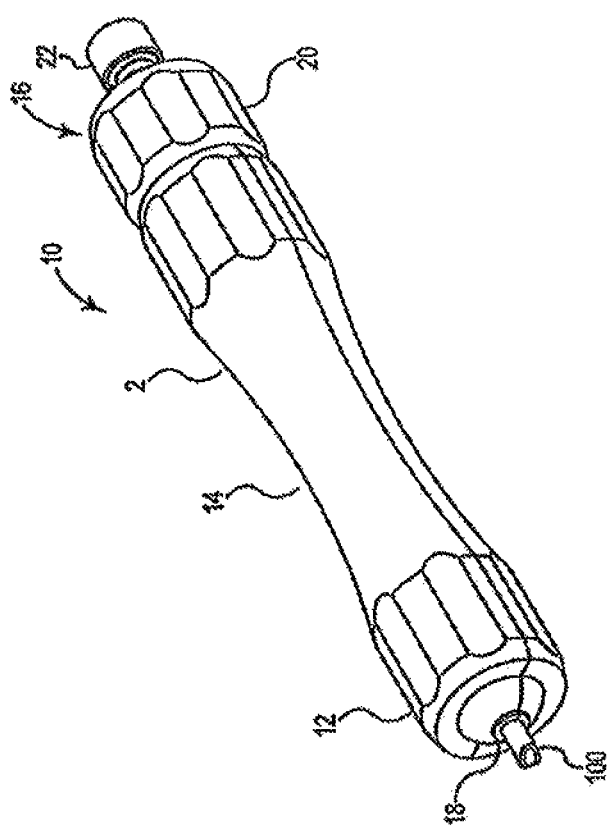
FIG. 1 is a perspective view of a control handle that may be operably coupled with the steerable sheath according to an aspect of the invention.

Numerous structural variations of an MR compatible steerable elastomeric member sheath in accordance with the invention are contemplated and within the intended scope of the invention. Those of skill in the art will appreciate that the exemplary steerable elastomeric member sheath may be coupled to other types of steerable sheath shafts having control handles. Therefore, for purposes of discussion and not limitation, an exemplary embodiment of the MR compatible steerable elastomeric member sheath will be described in detail below.

Referring to the FIGS. like elements have been numbered with like reference numerals.

Referring now to FIG. 1, the control handle 10 in accordance with the invention includes a cover 2 as illustrated in FIG. 1. Cover 2 includes distal portion 12, hand-graspable middle region 14, and proximal end 16. Distal portion 12 includes aperture 18 through which steerable sheath shaft 100 exits. Proximal end 16 includes rotatable adjustment knob 20 and port 22. Rotatable adjustment knob 20 is operably coupled to a proximal end (not shown) of steerable sheath shaft 100 such that rotation of the knob causes movement of steerable sheath shaft 100 as hereinafter described. Port 22 includes an aperture therethrough for receiving a medical device such as by way of example an MR-compatible electrode circuit such as that disclosed in U.S. Publn. No. 2011/0046707, the entirety of which is hereby incorporated by reference.

Figure 2A:
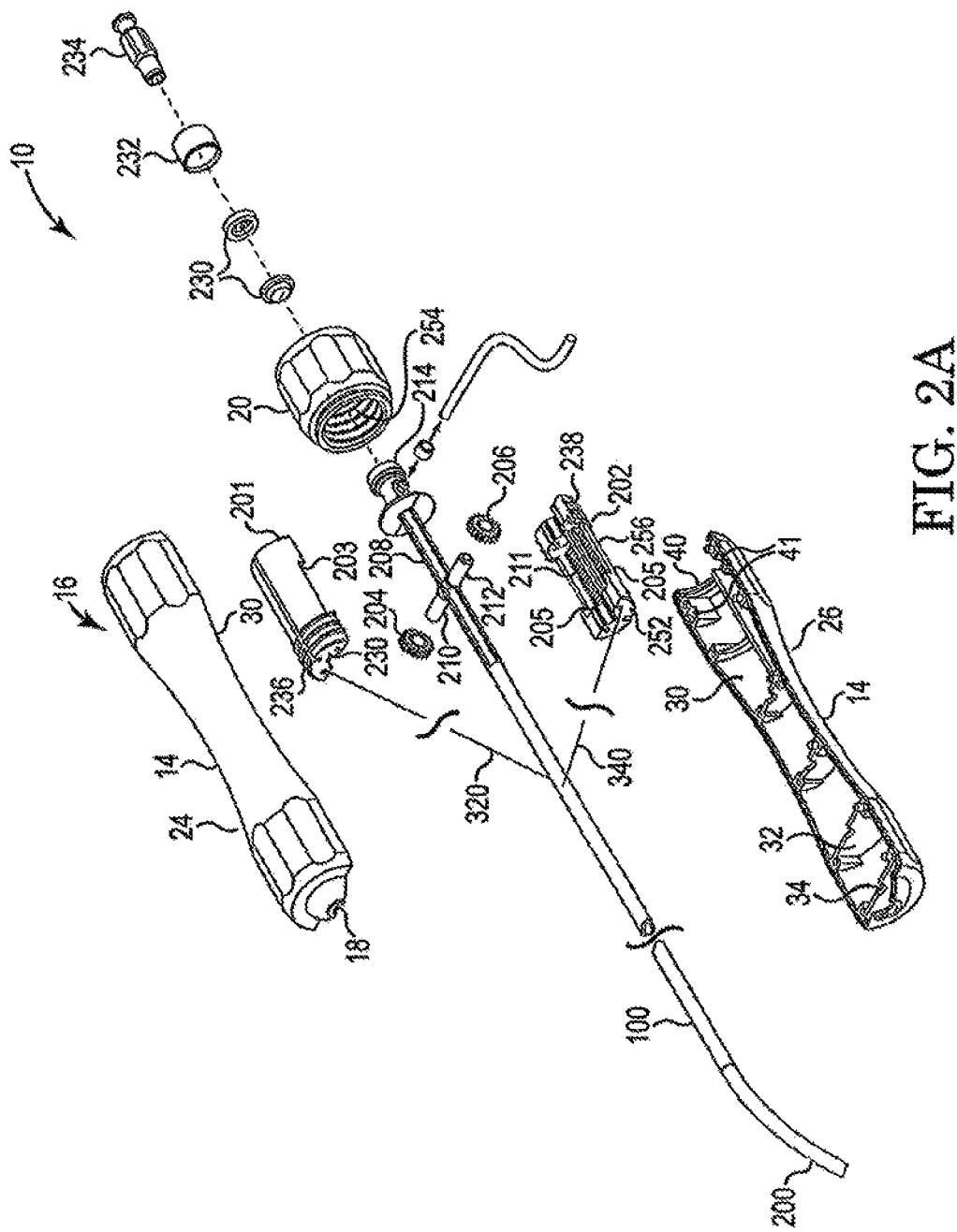
FIG. 2A is an exploded perspective view of the control handle and steerable sheath according to an aspect of the invention.

Referring now to FIG. 2A an exploded view of the control handle 10 and steerable sheath shaft 100 in accordance with the invention is shown. Cover 2 of control handle 10 includes a first mating portion 24 and a second mating portion 26. Those of skill in the art will appreciate, however, that cover 2 may include any number of mating portions and still be within the scope of the invention. Each of the first and second mating portions 24, 26 include an inner face 30 having a plurality of inserts 32 fixedly coupled to inner face 30. As depicted, inserts 32 include a receiving groove therewithin. When first mating portion and second mating portion are operably coupled, receiving groove 34 forms a lumen into which steerable sheath shaft 100 is received. First mating portion 24 and second mating portion 26 when mated form an internal recess 40 at a distal end thereof, which accommodates first and second rack screws 201, 202. It should be noted that the distal threads 236 of the first rack screw 201, although shown, have no function. First and second rack screws 201, 202 are simply mirror images of each other and the distal threads 236 of the first rack screw 201 are present to reduce the cost of manufacturing so that first and second rack screws 201, 202 can be made from the same mold. Control handle 10 further includes first and second pinion gears 204, 206, t-valve axle 208, first and second pegs 210, 212, t-valve 214, tube retainer 216, tube 218, and rotatable adjustment knob 20. Rotatable adjustment knob 20 receives seals 230, seal cap 232 and fitting 234. First and second pegs 210, 212 are operably coupled to t-valve axle 208. Groove 41 receives pegs 210, 212. First and second pegs 210, 212 receive pinion gears 204 and 206. Tube 218 attaches to a stopcock in t-valve which connects to a syringe for flushing or aspirating the steerable catheter.

As may be seen in FIG. 2A, second rack screw 202 includes proximal threads 238 on an outer surface thereof. Those of skill in the art will appreciate that "first" and "second" rack screws are relative terms. Those of skill in the art will also appreciate that the control knob 20 may be positioned distally to first and second rack screws and the orientation of first and second rack screws flipped as will be described below with reference to FIG. 2B. An internal central channel of each of first and second rack screws 201, 202 includes a threaded portion 211 that threadably receives pinion gears 204, 206 in operation. First and second rack screws 201, 202 include notched portion 203, 205. First and second pull wires 320, 340 are routed and are operably coupled to ends 230, 252 of each rack screw 201, 202, respectively. Pinion gears 204, 206 are received by pegs 210, 212 operably coupled to t-valve axle 208. T-valve axle 208 is bonded to sheath shaft 100. In operation, posts 210, 212 are received by and move longitudinally on notched portion 203, 205 respectively. This allows threaded pinion gears 204, 206 to be received by and move longitudinally along the threaded central channel of each of first and second rack screws 201, 202.

As seen in FIG. 2A, rotatable adjustment knob 20 includes internal threads 254 circumferentially disposed about an inner wall thereof. Internal threads 254 will engage the proximal threads 238 of the second rack screw 202. As the rotatable adjustment knob is rotated clock-wise the internal adjustment knob threads 254 engage the proximal threads 238 of the second rack screw 202 causing longitudinal, proximal movement of rack screw 202. As the rotatable adjustment knob is rotated counter-clockwise the internal threads (still engaged with the proximal threads 238 of the second rack screw 202) causes longitudinal, distal movement of rack screw 202.

Those of skill in the art will appreciate that the orientation of the first and second rack screws may be changed without departing from the scope of the invention. As may be seen in FIG. 2B, second rack screw 202' includes distal threads 238' on an outer surface thereof. An internal central channel of each of first and second rack screws 201', 202' includes a threaded portion 211' that threadably receives pinion gears 204', 206' in operation. First and second rack screws 201', 202' include notched portion 203', 205'. First and second pull wires (not shown) are routed and are operably coupled to ends 230', 252' of each rack screw 201', 202', respectively. Pinion gears 204', 206' are received by pegs 210', 212' operably coupled to t-valve axle 208'. T-valve axle includes a lumen therewithin that slidably receives sheath shaft 100' at a distal end thereof. In operation, posts 210', 212' are received by and move longitudinally on notched portion 203', 205' respectively. This allows threaded pinion gears 204', 206' to be received by and move longitudinally along the threaded central channel of each of first and second rack screws 201', 202'.

As seen in FIG. 2C, rotatable adjustment knob 20' includes internal threads 254' circumferentially disposed about an inner wall thereof. Internal threads 254' will engage the distal threads 238' of the second rack screw 202'. As the rotatable adjustment knob 20' is rotated clock-wise the internal adjustment knob threads 254' engage the distal threads 238' of the second rack screw 202' causing longitudinal, proximal movement of rack screw 202'. As the rotatable adjustment know is rotated counter-clockwise the internal threads (still engaged with the distal threads 238' of the second rack screw 202') causes longitudinal, distal movement of rack screw 202'. Thus, those of skill in the art will appreciate that although the rotatable adjustment knob 20' is positioned distal to the first and second rack screws 201', 202' the operation of the control handle has not changed.

Figure 10:
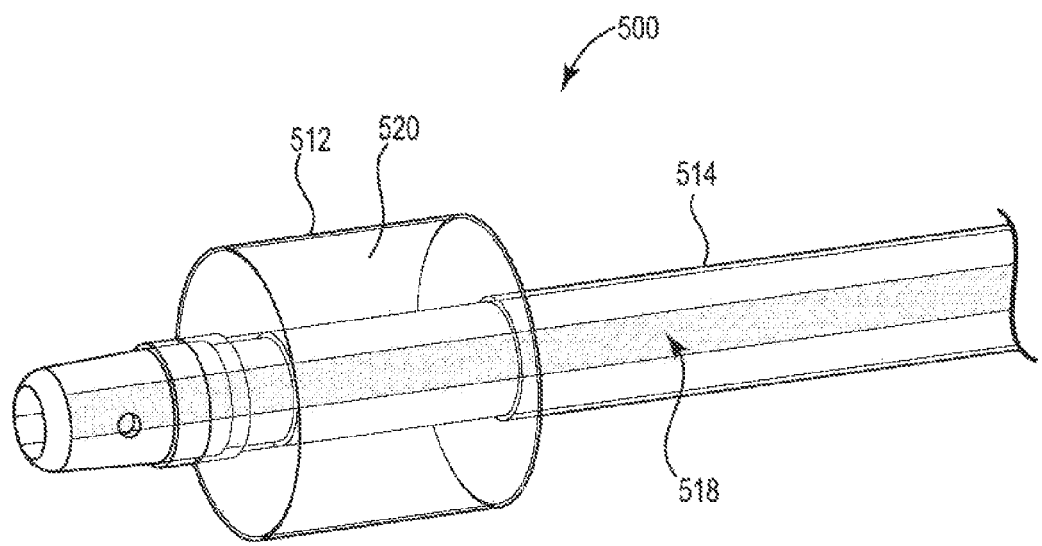
FIG. 10 is a perspective view of the steerable sheath with a circular shaped elastomeric member circumferentially surrounding the outer diameter of the sheath at a distal end thereof.

Rotatable adjustment knob 20' of FIGS. 2B and 2C includes grooves 500 on an outer surface thereof which, in operation, accommodate a plurality of O-rings 510 (as best seen in FIG. 10) that create a friction fit between the knob 20' and the first mating portion 24' and second mating portion 26' of cover 2 of control handle 10, which has corresponding grooves.

Figure 3:
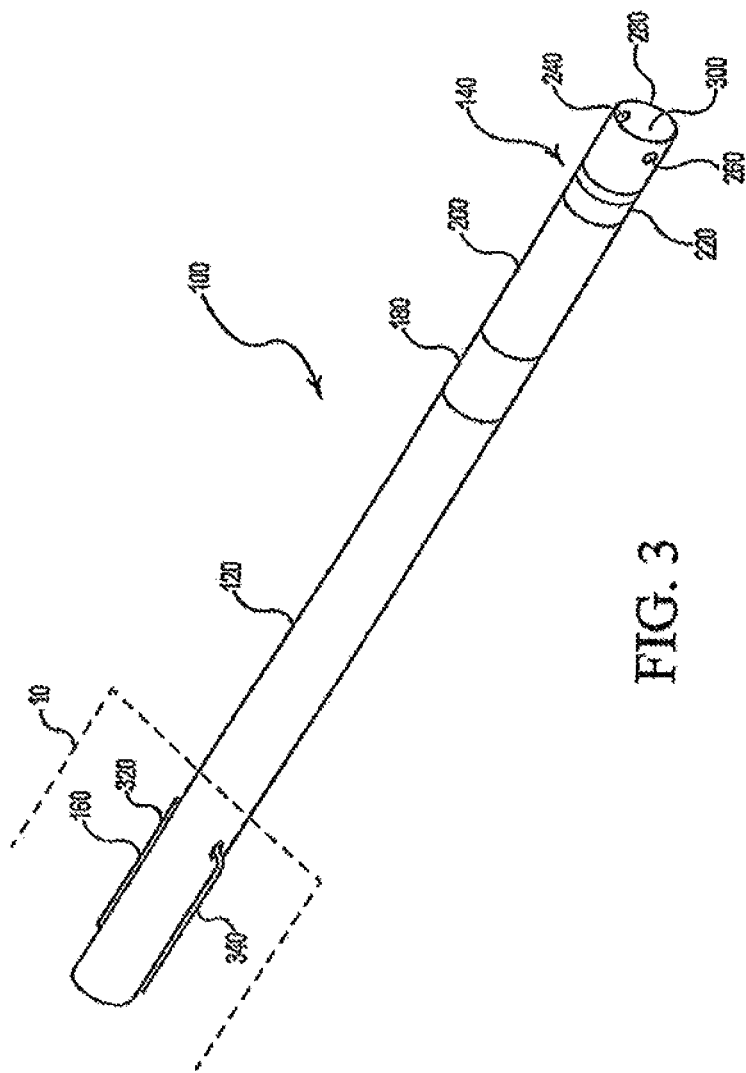
FIG. 3 is a perspective view of the steerable sheath shaft according to an aspect of the invention.

Referring now to FIG. 3, the steerable sheath shaft 100 in accordance with the invention will now be explained. Steerable sheath shaft 100 may be used in an MRI environment to deliver a variety of tools such as catheters, guide wires, implantable devices, etc. into cavities and passageways of a patient body. The steerable sheath shaft 100 includes a deflectable tip portion 200 that is able to bend at least 180 degrees offset from the longitudinal axis of the catheter sheath shaft 100. This flexibility allows the medical professional to make very tight turns to deliver the aforementioned tools to the cavities and passageways of the patient body.

Referring again to FIG. 3 a perspective view of an MR compatible steerable sheath that is suitable for use in an MRI environment is depicted. The MR compatible steerable sheath shaft 100 in accordance with the invention broadly includes tubular shaft 120 with distal 140 and proximal ends 160. Tubular shaft 120 includes an outer diameter 130, an inner diameter 150 and defines a central lumen 300 therewithin. Tubular shaft may be constructed of a variety of polymers such as pebax, polyurethane, nylon, derivatives thereof and combinations of the foregoing.

Distal end 14 includes transition section 180, deflectable tip portion 200, and magnetic marker 220. Pressure relief holes 240, 260 may be formed in the tubular shaft 120 at the distal end 140. Those of skill in the art will appreciate that while only two pressure relief holes 240, 260 are shown there may any number of pressure relief holes formed and still be within the scope of the invention. When retracting an item housed by the sheath shaft 100, such as a catheter or MR active tracking system, pressure may form at the end of the sheath thereby drawing or sucking in tissue. Pressure relief holes 240, 260 are designed to reduce this pressure thereby ameliorating the risk of tissue damage.

Transition section 180 is optionally included for purposes of manufacturability. The deflectable tip section 20 has a significantly lower durometer making it more malleable and flexible than the main body portion 170 of tubular shaft 120 which has a higher durometer or, in other words, quite stiff. As a consequence, these two sections do not bond to one another well. Transitional section 180 has a mid-range durometer allowing it to bond well to both the deflectable tip section 200 and the main body 170 of the tubular shaft 120.

Those of skill in the art will appreciate that the transition section 180 may be of any length desired so as to provide an adequate transition between the distal tip portion 200 and the main body portion 170. In one exemplary embodiment transition section may range from about 0.25 to about 0.75 inches. In addition, those of skill in the art will appreciate that transition section may be eliminated and the deflectable tip section 200 may be coupled to the main body 170 of tubular shaft 120 by means known to those of skill in the art without departing from the spirit of the invention.

Steerable sheath shaft 100 includes central lumen 300 therewithin. In one aspect of the invention, the inner diameter 150 of the tubular shaft 120 is approximately 6 French or greater but those of skill in the art will appreciate that varying internal diameters may be used depending on the particular application without departing from the scope of the present invention. Central lumen 300 may include one or more liners (not shown) disposed therewithin to allow for easier movement of instruments therethrough. Liners may comprise materials made from polytetrafluoroethylene (PTFE), fluorinated ethylene propylene copolymer (FEP), nylons and combinations of the foregoing. Alternatively, the lumen 300 may be coated with any such polymers. The polymer tubular shaft 120 may also include one or more passive visualization markers, such as a ferrous or magnetic marker 220, disposed circumferentially about the tubular shaft 120 at one or more locations along the length thereof and/or one or more active visualization markers such as an active tracking coil along the length of the tube. An active tracking coil may comprise one or more small antennas integrated into the device and include traces on a circuit board, coiled wire, and/or a dipole. If an active visualization marker is used, one or more devices may be included in the conductors to mitigate RF field heating may be included. Such devices include chokes, transformers, impedances, and other such devices known to those of skill in the art. One or more fluoroscopy markers (not shown) may also be included along the length of the polymer tubular shaft 12.

One or more optional fluid ports (not shown) may be located on the proximal end 16 of the tubular shaft 12 to allow for homeostasis of the sheath with the patient body. The fluid port(s) allows access for the user or physician to aspirate blood from the steerable sheath lumen 30 and flush with saline. Aspirating and flushing of the sheath prevents air from entering the body before and during insertion of a tool and/or catheter.

Figure 4:
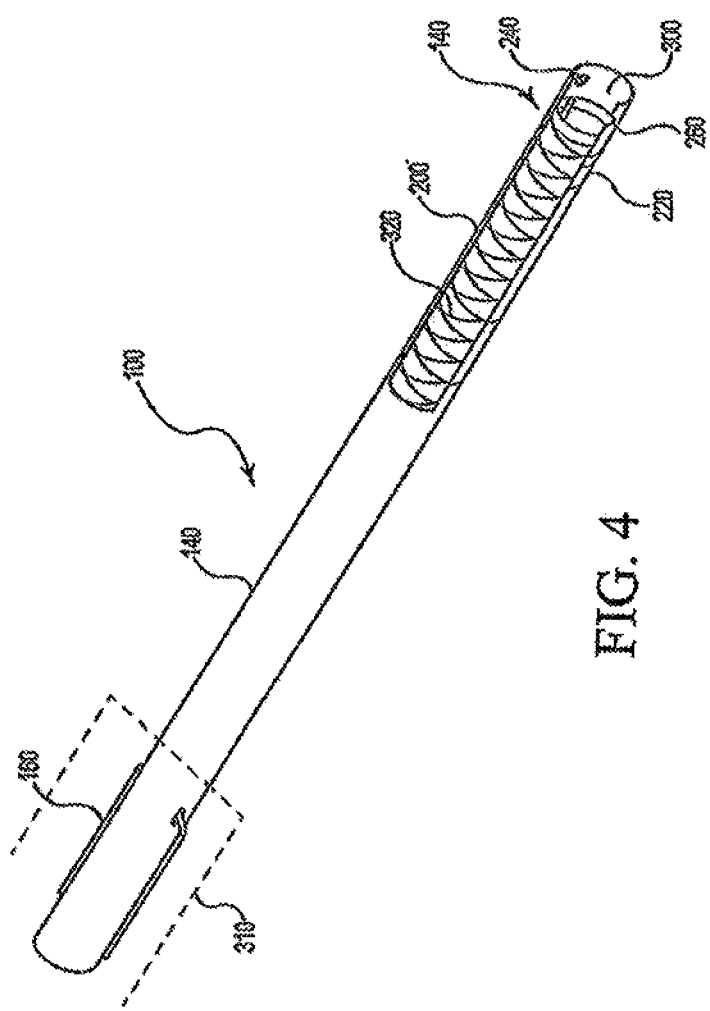
FIG. 4 is a perspective view of the steerable sheath shaft according to an aspect of the invention with the steerable distal tip cut away to show detail.

Referring now to FIG. 4 a cut away view of the steerable sheath shaft 100 in accordance with the invention depicts a reinforcement construct 320 of the tubular shaft 120. As shown, the geometry of the reinforcement construct 320 is braided but those of skill in the art will appreciate that the reinforcement construct 320 may comprise other configurations so long as it imparts the necessary deflectability to the tubular shaft 120 at the distal end. For example the reinforcement geometry may be a coil or a slit tube that mimics a coil or combinations of the foregoing. The reinforcement of the tubular shaft 120 may extend from the distal end 140 to the proximal end 160 or may extend from the deflectable tip section 200 to approximately the transition section 180 of the tubular shaft 12.

The material used in the reinforcement construct 320 may be non-metallic such as Kevlar, PEEK, Nylon, fabric, polyimide, fiber optic, silica glass and the like or may also be hybrid of metallic, such as stainless steel, and non-metallic materials. Those of skill in the art will appreciate that, the reinforced polymer tubular shaft 140 may be segmented and each segment may be constructed with varying flexibility along the segment to provide the user with the ability to deflect the sheath in a region in which the segment is more flexible than in other segments. Varying flexibility and thus deflectability may be accomplished by having braids or coils that have greater braiding or coils per sq. cm than in other segments where the braiding or coiling would be less per sq. cm. Flexibility and deflectability may also be accomplished by the varying durometers as herein described.

Referring now to FIG. 5A, an enlarged view of the proximal end 160 of the steerable sheath shaft 100 in accordance with the invention is depicted. Proximal end 160 of the steerable sheath is operably coupled to control handle 10 depicted in dashed lines and as hereinafter described. The steerable sheath shaft 100 in accordance with the invention includes one or more pull-wires 320, 340 which are operably coupled at a pull-wire proximal end 342 to the control handle 10 as hereinafter will be described. The portion of the pull-wires 320, 340 that are operably coupled to the control handle exit the tubular body 120 at opening 122. The portion of the pull-wires 320, 340 that are operably coupled to pull ring 440 (as best seen in FIG. 5B) extend through a lumen constructed from a sheet of polymeric material fastened to an inner portion of tubular shaft 120 for a length thereof and enter tubular shaft 120 through entrance holes 330, 350 on opposing sides of tubular shaft 120. Pull-wires 320, 340 allow the user to manipulate and deflect the one or more flexible segments along the length of the polymer tubular shaft 120 and in particular the deflectable tip portion 200. In one aspect of the invention, the pull-wires 320, 340 are preferably made of a non-metallic material (Kevlar, PEEK, Nylon, fabric, etc.).

One or more internal pull-wire lumens 360 are constructed of a flexible, non-metallic material such as PTFE. Internal pull-wire lumens 360 facilitate smooth manipulation of the pull-wires 320, 340 during actuation. Internal pull-wire lumens 360 have an outer diameter of approximately 0.12 inches and an inner diameter of approximately 0.010 inches. However, those of skill in the art will appreciate that the dimensions of the internal pull-wire lumens 360 may vary with the dimensions of both the pull-wires 320, 340 and the tubular shaft 120 so long as they are dimensioned to house the pull-wires and allow pull-wires to move smoothly during actuation.

Referring to FIG. 5B, a side view of the distal end of the steerable sheath in accordance with the invention is shown. Pull wires 320, 340 are operably coupled at their distal end to an opening 440 in pull ring 442 positioned within lumen 300 at the deflectable tip 200 end of the steerable sheath shaft 100.

Referring now to FIGS. 6-9 an exemplary control handle 31 for operating the steerable sheath is disclosed. As discussed in reference to FIG. 2, control handle 310 allows the user to control the longitudinal movement of pull-wires 320, 340 which in turn "pull" or deflect the distal end 140 of the steerable sheath shaft 100 in opposite directions. Control handle 310 is positioned on the proximal end of the steerable sheath shaft 100 and operates longitudinal movement of the pull-wire(s) and correspondingly, directional movement of the steerable sheath shaft 100. In one aspect of the invention, control handle 310 includes paramagnetic or diamagnetic materials or combinations of paramagnetic and diamagnetic materials.

Figure 6A:
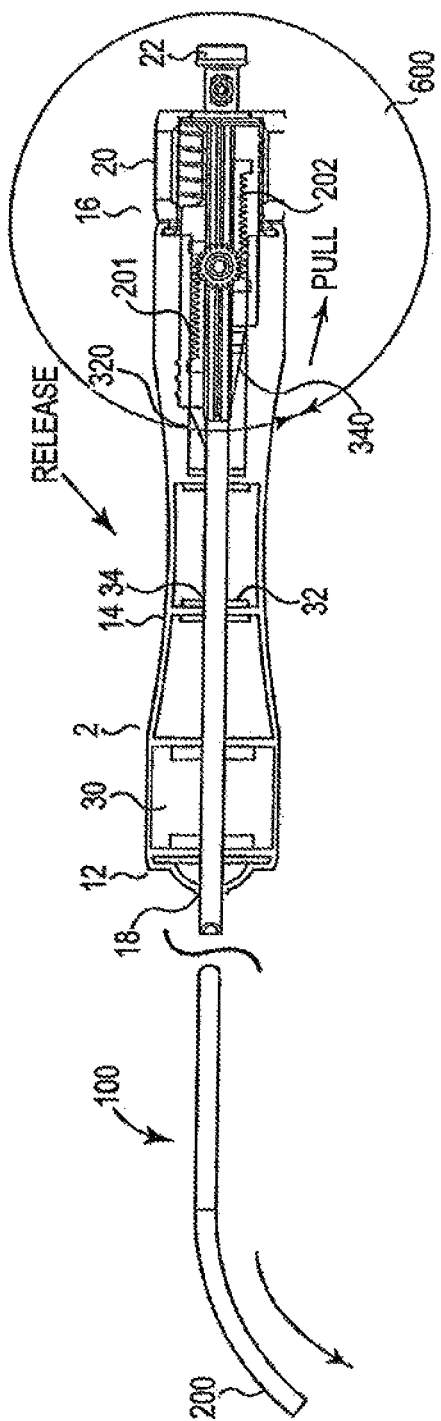
FIG. 6A is a side view of the control handle and steerable sheath of FIG. 2A.
Figure 6B:
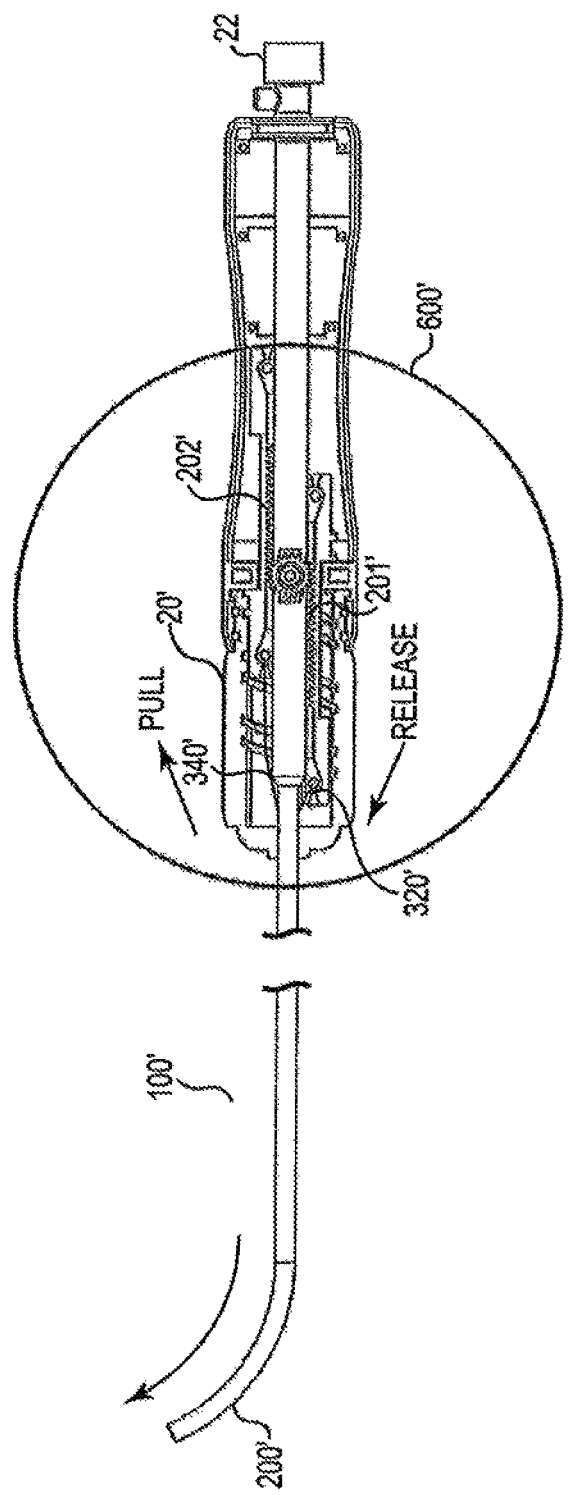
FIG. 6B is a side view of the control handle and steerable sheath of FIG. 2B.
Figure 7A:
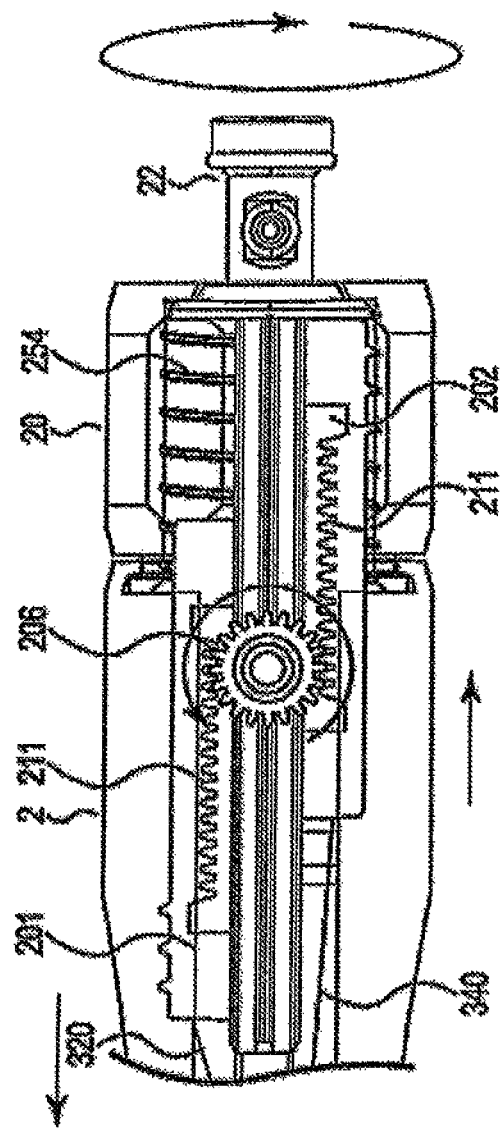
FIG. 7A is an enlarged view of the control handle mechanical structure denoted by 600 in FIG. 6A and showing clockwise rotation of rotatable knob.
Figure 7B:
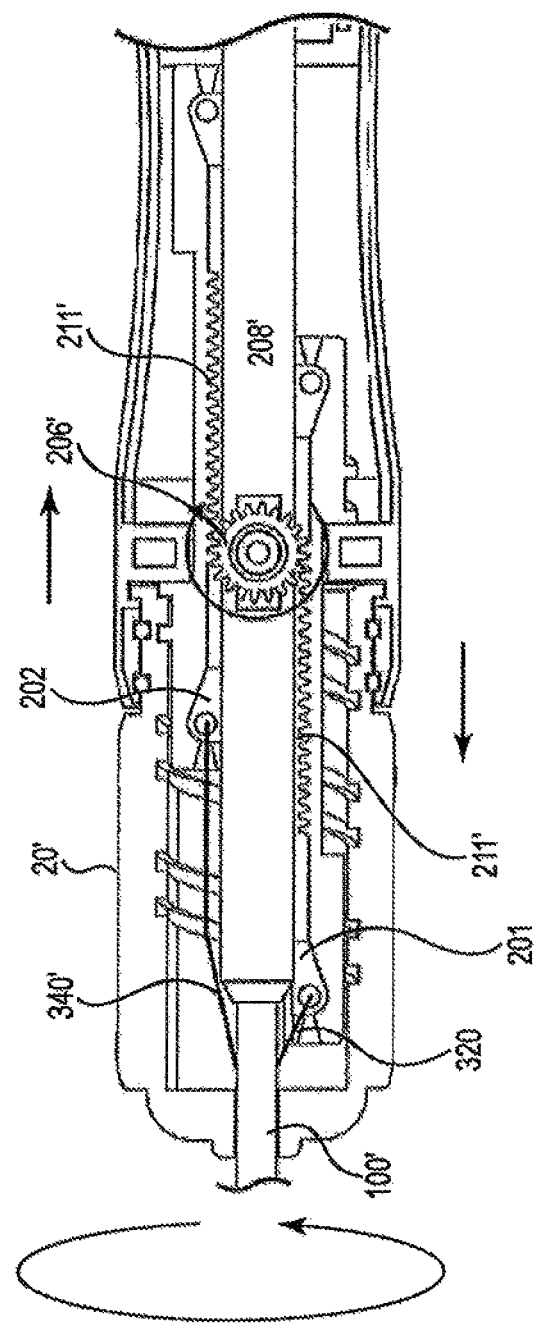
FIG. 7B is an enlarged view of the control handle mechanical structure denoted by 600' in FIG. 6B and showing clockwise rotation of rotatable knob.
Figure 8A:
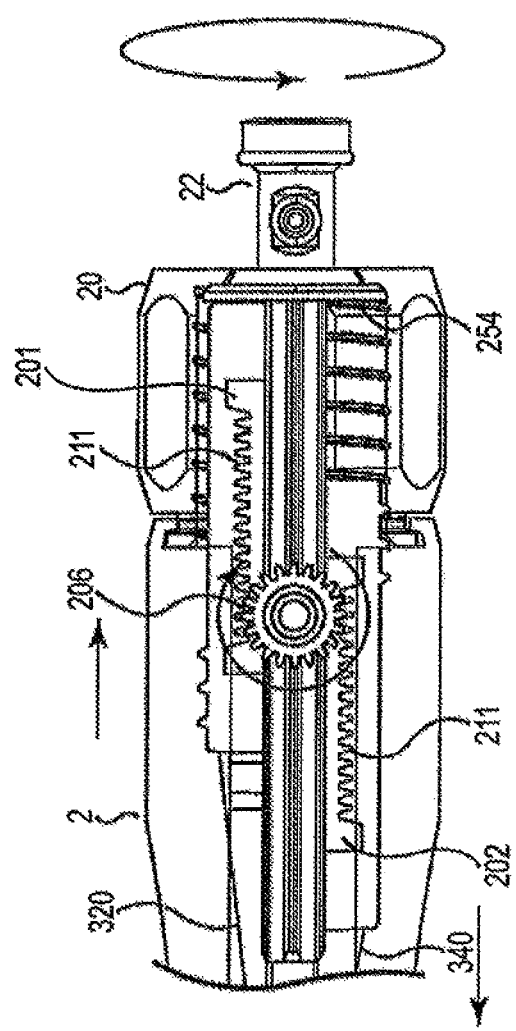
FIG. 8A is an enlarged view of the control handle mechanical structure denoted by 800 in FIG. 6A and showing counterclockwise rotation of rotatable knob.

Referring now to FIGS. 6A-7B, FIGS. 7A and 7B are enlarged views of the control handle of FIGS. 6A and 6B denoted at numeral 600, 600'. Adjustment knob 20, 20' is rotated in the clockwise direction, which causes internal threads 254, 254' to engage threads 238, 238' of second rack screw 202, 202' and cause longitudinal, proximal movement of the second rack screw 202, 202'. At the same time, the pinion gears are engaged by the longitudinal movement of the second rack screw 202, 202'. This causes the first rack screw 201, 201' to move in the opposite direction, i.e. distally. Distal movement of the first rack screw 201, 201' releases tension in the first pull wire 320, 320'.

As rotatable adjustment knob 20, 20' is rotated in the clockwise direction and engages rack screws which in turn engage pinion gears, second pull wire 340, 340' is pulled toward the proximal direction as best seen in FIGS. 6A and 6B. In turn, the tension on first pull wire 320, 320' is released. As second pull wire 340, 340' is pulled in the proximal direction deflectable tip moves in one direction, shown as a downward direction in FIG. 6A and an upward direction in FIG. 6B; however those of skill in the art will appreciate that the direction of deflectable tip is relative to how or the direction in which the user is holding the handle 10. When the t-valve pegs 210, 210', 212, 212' abut stops 205, 205' in second rack screw 202, 202' the rack screw 202, 202' stops moving and further movement of rotatable adjustment knob 20, 20' is halted.

Referring now to FIGS. 8A, 8B and 9A, 9B the opposite function is illustrated. Adjustment knob 20, 20' is rotated in the counter-clockwise direction, internal threads 254, 254' engage threads 238, 238' of second rack screw 202, 202' causing longitudinal, distal movement. As the rotatable adjustment knob 20, 20' continues to be rotated in a counter-clockwise direction, pinion gears 204, 204', 206, 206' once again operably engage threaded portion 211, 211' of first and second rack screws.

Figure 9A:
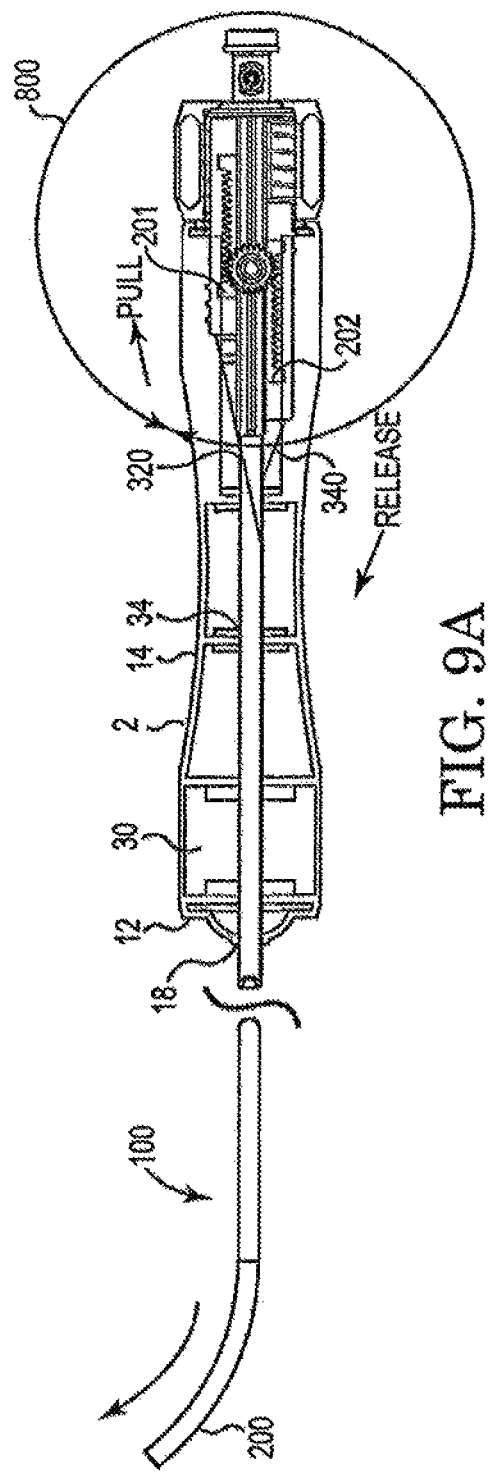
FIG. 9A is a side view of the control handle of FIG. 2A showing the function of the pull wire.
Figure 9B:
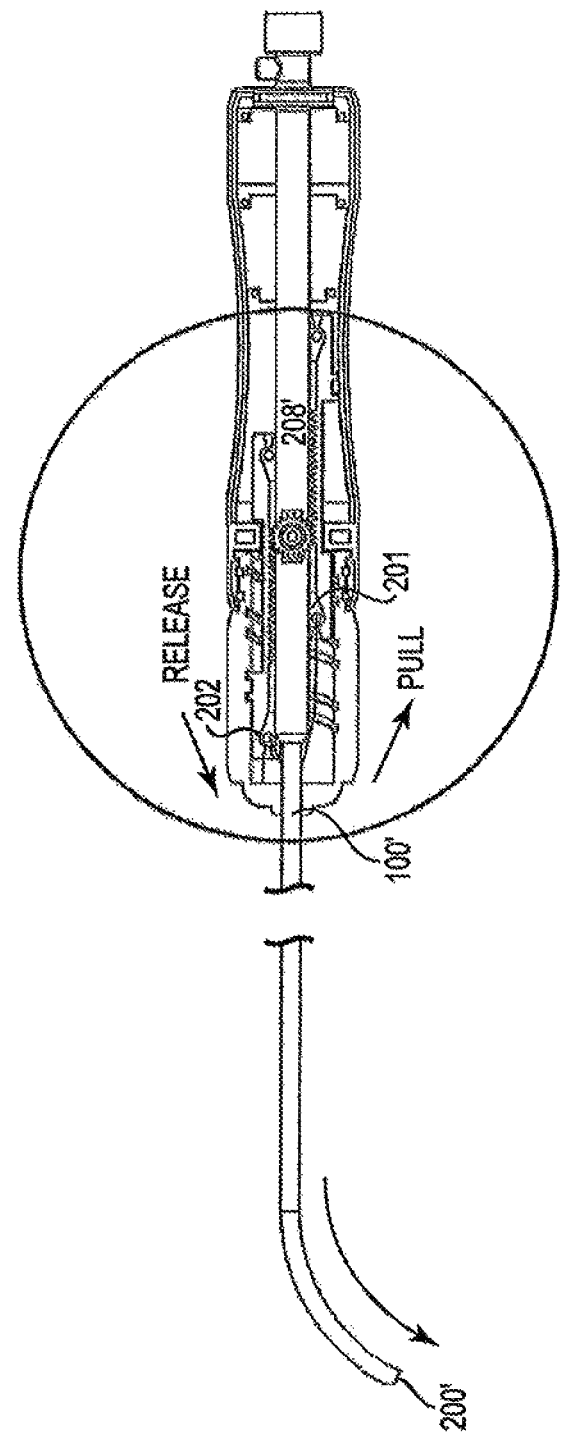
FIG. 9B is a side view of the control handle of FIG. 2B showing the function of the pull wire.

As rotatable adjustment knob 20, 20' is rotated in the counter-clockwise direction first pull wire 320, 320' is pulled toward the proximal direction as best seen in FIGS. 9A and 9B. In turn, the tension on second pull wire 340, 340' is released. As first pull wire 320, 320' is pulled in the proximal direction deflectable tip moves in the opposite direction, shown as an upward direction in FIG. 9A and a downward direction in FIG. 9B; however those of skill in the art will appreciate that the direction of deflectable tip is relative to how, or the direction in which, the user is holding the handle 10. When the t-valve pegs 210, 210', 212, 212' abut stops 205, 205' in second rack screw 202, 202' the rack screw 202, 202' stops moving and further movement of rotatable adjustment knob 20, 20' is halted.

Referring now to FIGS. 10-23, the control handle and steerable sheath shaft of FIGS. 1-9 has been modified to include a distally located elastomeric member 500 in accordance with the invention. An exemplary embodiment will use control handle 10' of FIG. 2B to describe the invention. The integration of an elastomeric member onto the steerable sheath in accordance with the invention creates a reservoir for the injection of an MRI contrast agent. When the contrast agent is injected into the elastomeric member, the elastomeric member expands and becomes visible on the image generated during the MRI scan. During this process, the sheath, otherwise invisible on the MRI scan, is rendered visible at the location of the contrast filled elastomeric member. Those of skill in the art will appreciate that this technique may also be utilized with a therapy catheter and the like. Like elements in the Figures are labeled with like reference numerals.

Figure 11:
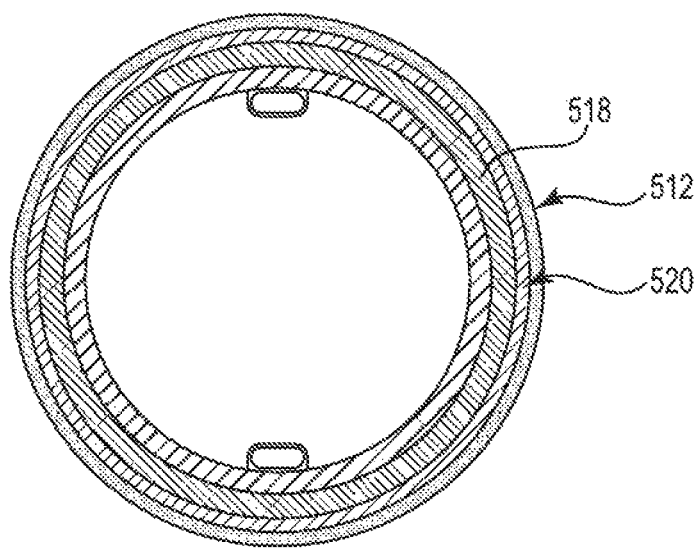
FIG. 11 is a cross-sectional view of the shaft and elastomeric member of FIG. 10.
Figure 13:
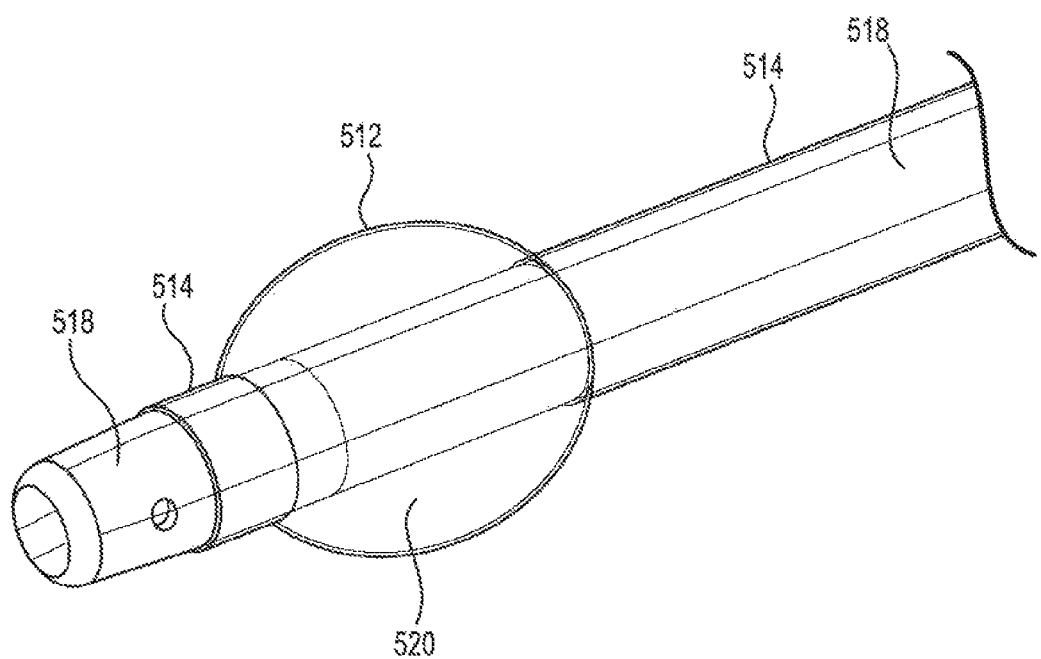
FIG. 13 is a perspective view of a spherical-shaped elastomeric member circumferentially surrounding the steerable sheath at a distal end thereof.
Figure 14:
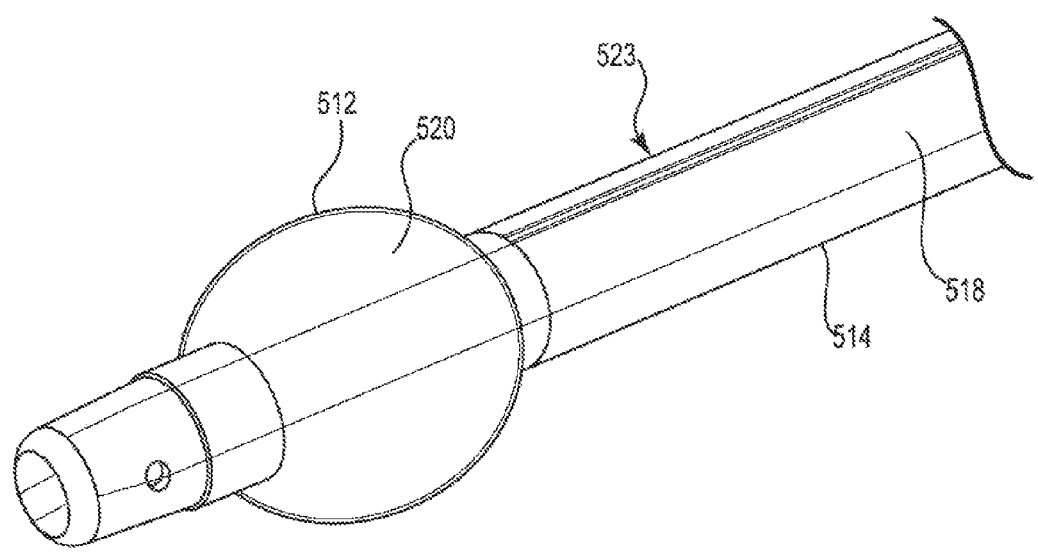
FIG. 14 is a perspective view of the spherical-shaped elastomeric member of FIG. 13 depicting a single tube lumen access to the elastomeric member.
Figure 16:
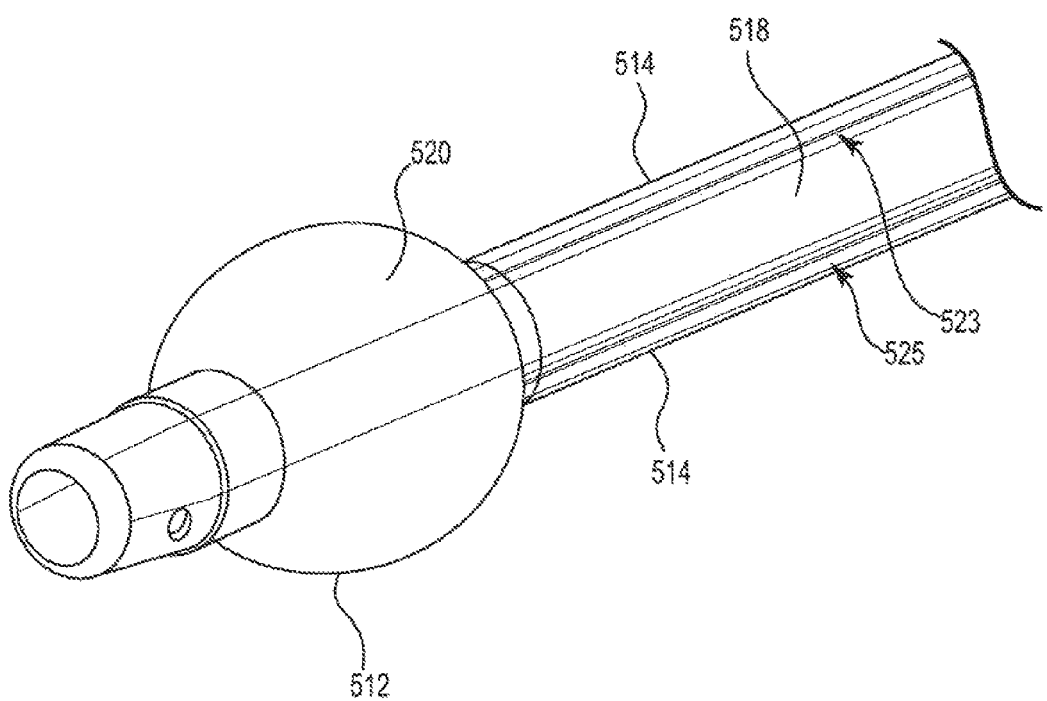
FIG. 16 is a perspective view of a steerable sheath including an elastomeric member depicting two tube lumen access to the elastomeric member.
Figure 17:
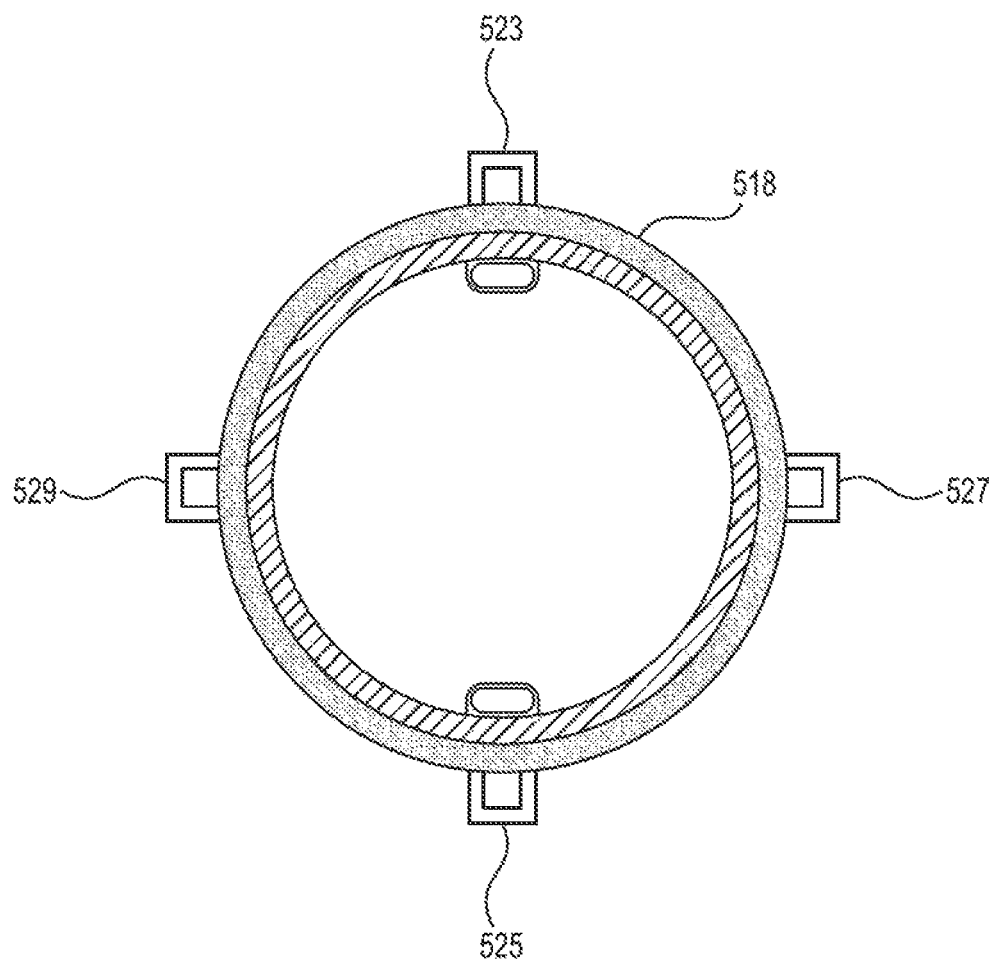
FIG. 17 is a cross-section view of an elastomeric member showing multiple tube lumen access to the elastomeric member.

Referring now to FIG. 10, a first aspect of the deflectable sheath with elastomeric member 500 in accordance with the invention is shown. Elastomeric member 512 circumferentially encompasses the outer diameter of the sheath shaft 518. The elastomeric member 512 includes an axially extending sheath portion 514 which surrounds the sheath shaft 518 and creates a lumen coupled to a source of contrast media at one end and is in fluid communication with lumen 520 at a second opposing end. The shape of the elastomeric member 512 may be one of many including, but not limited to, circular, conical, square, spherical, elliptical, tapered, dog bone, paddle, offset as best seen in FIGS. 10 through 23. In one aspect as best seen in FIG. 11 the elastomeric member 512 may circumferentially surround the outer diameter of the sheath shaft 518. In another aspect, as best seen in FIGS. 14 and 17, the elastomeric member lumen 520 may comprise one or more tubes 523, 525 that extend along the longitudinal axis of the sheath shaft 518 and are bonded or otherwise operably coupled thereto. The tubes 523, 525 form a lumen that in is fluid communication at one end with a source of contrast media and with lumen 520 of elastomeric member 512 at an opposing end. The elastomeric member 512 and sheath portion 514 may be integrally or non-integrally formed. With respect to non-integrally formed embodiments fastening or anchoring the elastomeric member 512 to the sheath portion 514, numerous techniques may be utilized including heat shrinking the elastomeric member 512 onto the sheath portion 514, joining the elastomeric member 512 to the sheath portion 514 with adhesive, mechanical means, thermal molding of the elastomeric member 512 onto the sheath portion 514 and other methods known to those of skill in the art. In the foregoing embodiments the elastomeric member 512 and sheath portion 514 may comprise the same material or may comprise different materials. Alternatively, the sheath 514 and elastomeric member 514 may be integrally formed and be of the same material.

Figure 12:
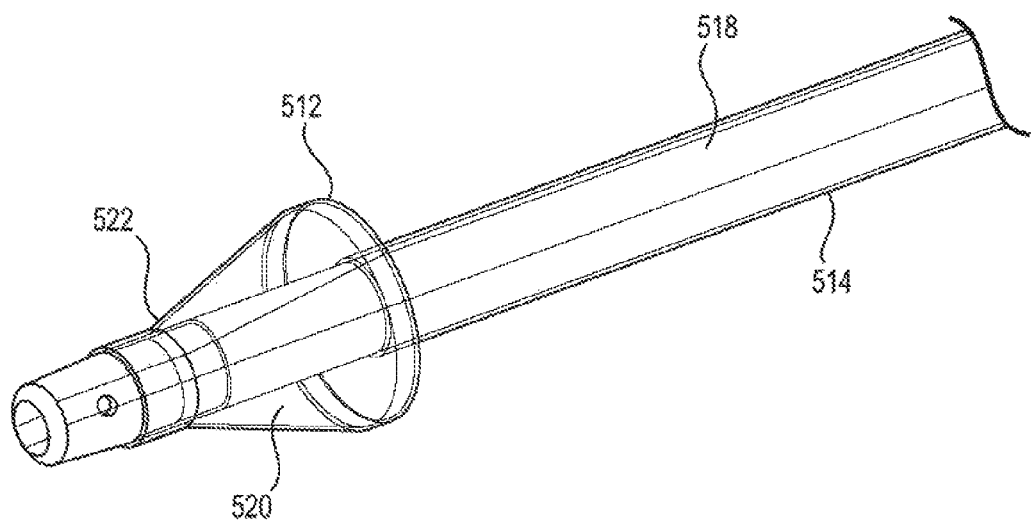
FIG. 12 is a perspective view of a conical-shaped elastomeric member circumferentially surrounding the steerable sheath at a distal end thereof.
Figure 15:
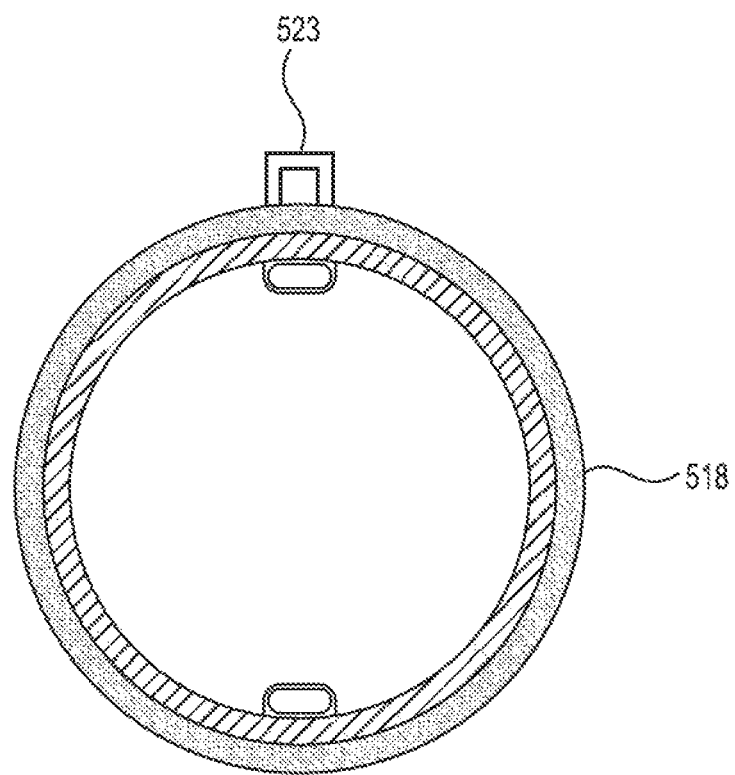
FIG. 15 is a cross-sectional view of the device shown in FIG. 14.

A conical shaped elastomeric member 512 is seen in FIG. 12. The conical shaped has a tapered-end 522 at the most distal portion of the sheath portion 514. Alternatively, the conical shaped elastomeric member 512 may be coupled to the sheath shaft 518 and tubes 523, 525 (a single tube or multiple tubes) may fluidly couple lumen 512 to a source of contrast media. When the elastomeric member 512 receives contrast media within lumen 520, the tapered-end 522 may indicate the direction of steerable sheath 500 when in use. FIG. 13 depicts a spherical-shaped elastomeric member circumferentially surround the steerable sheath at a distal end thereof. FIG. 14 depicts the spherical-shaped elastomeric member of FIG. 13 with a single tube lumen 523 fluidly coupled to elastomeric member lumen 520 at a first end 525 and fluidly coupled to a source of contrast media at a second end. FIG. 15 is a cross-section of the device of FIG. 14 showing the single tube lumen 523. FIG. 16 depicts the spherical-shaped elastomer member 512 of FIG. 13 showing two tube lumen access 523, 525 to the lumen 520 of elastomeric member 512. FIG. 17 is a cross-sectional view depicting multiple tube lumen access 523, 525, 527, 529 to the lumen 520 of elastomeric member 512.

Figure 18A:
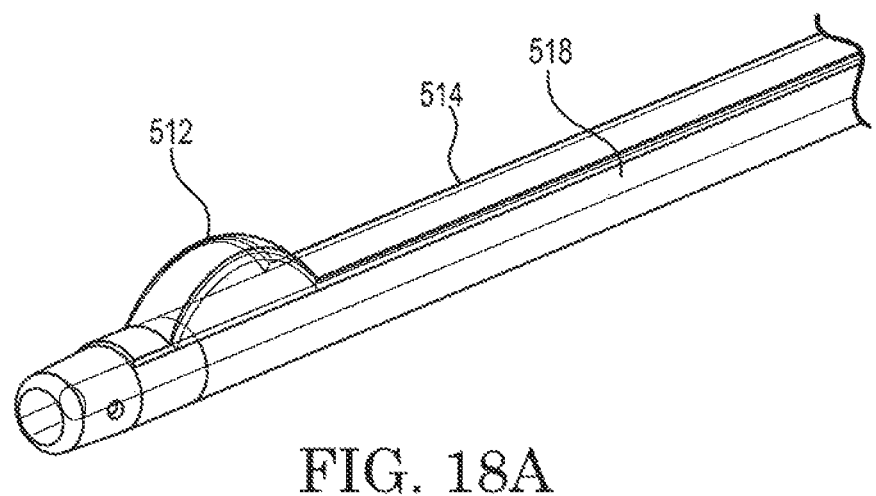
FIGS. 18A-18C are perspective views of elastomeric members that are offset along a longitudinal axis of the steerable sheath.
Figure 18B:
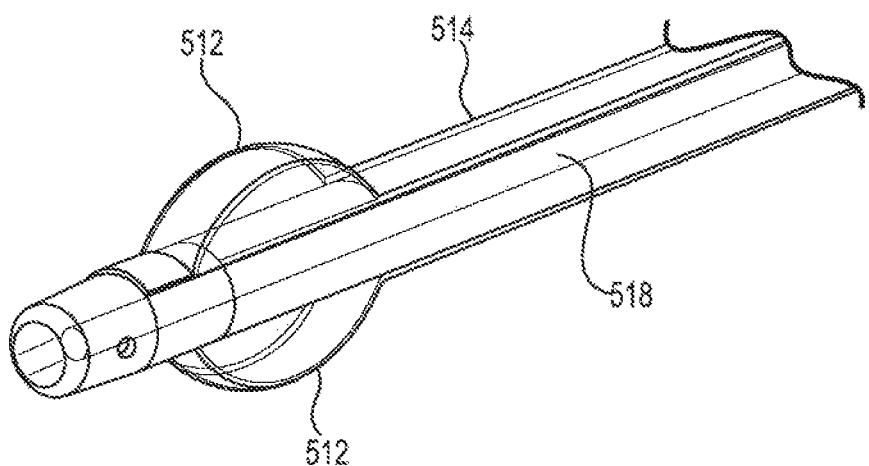
Figure 18C:
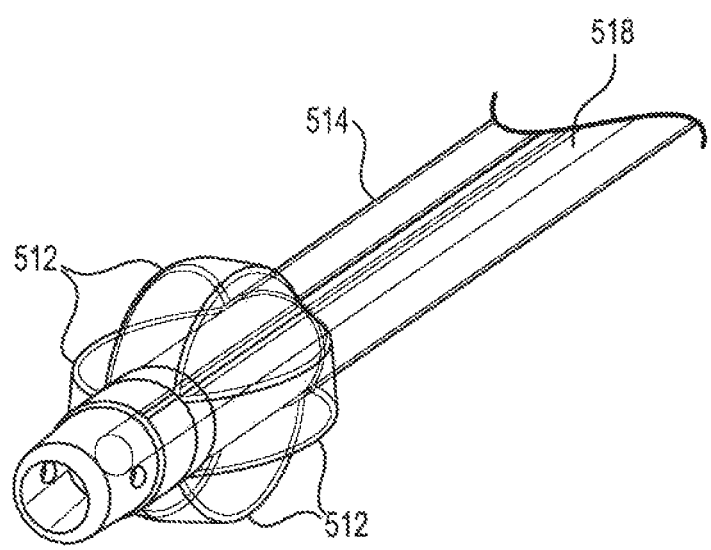

As best seen in the FIGS. the elastomeric member 512 or multiple elastomeric members may be located at the most distal tip of the sheath 512 proximate the deflection region of the sheath shaft 518. Referring now to FIG. 18A a single elastomeric member 512 offset from the longitudinal axis of the sheath shaft 518 is shown. Multiple elastomeric members may be offset from the longitudinal axis of the sheath 514 as best seen in FIGS. 18B and 18C. Locating the elastomeric members 512 in a non-circumferential location on sheath shaft 518 may impart additional geometrical information to the clinician. For example, the two elastomeric members 512 that are 180 degrees opposed, as best seen in FIG. 18B, may be positioned such that their shapes are in plane with the deflection plane of the steerable sheath 100', and therefore the clinician may discern more information about the steerable sheath 100' than just the location of the deflectable tip 200'. The same could be said of locating just a single offset balloon to one side of the sheath shaft 518 and in plane with the deflection plane of the steerable sheath 100'.

Figure 20:
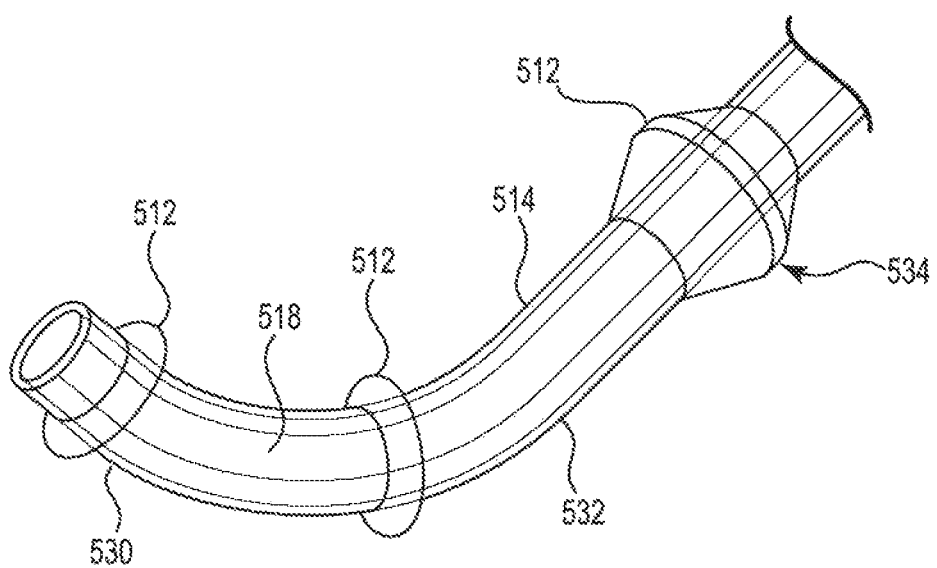
FIGS. 20-21 are perspective views of a deflectable sheath including multiple elastomeric members.
Figure 21:
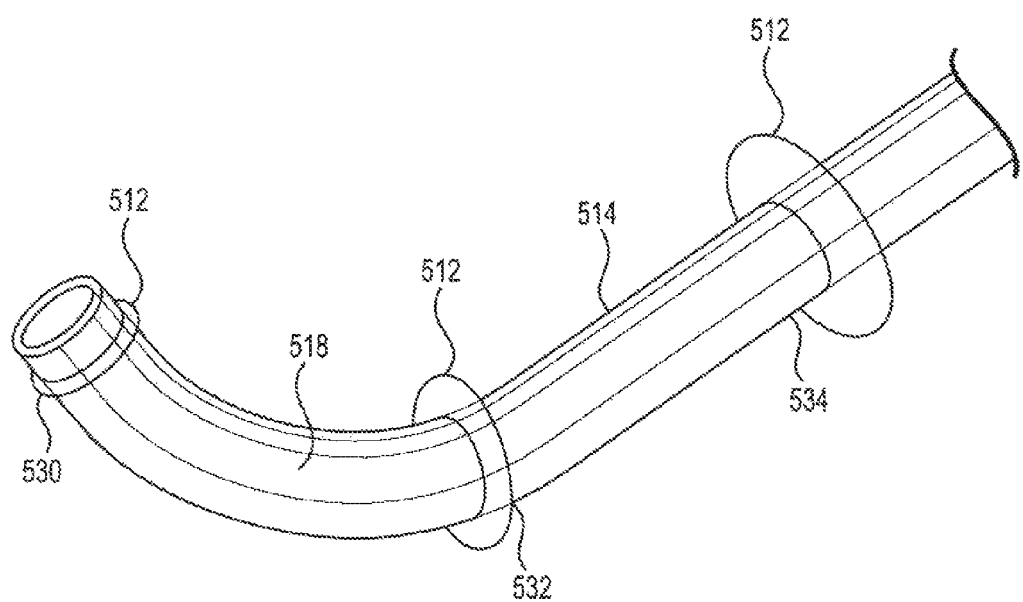

FIGS. 19A and 19B depict the deflection region 531 of the sheath shaft 518. Referring now to FIGS. 20 and 21 multiple elastomeric members 512 may be utilized to indicate the direction of the steerable sheath shaft 518. As seen in FIGS. 20-21, curve shape and direction may be indicated on the MR image by different elastomeric member shapes. This would be accomplished by locating the elastomeric members 512 at different positions on the distal section of the sheath shaft 514. For example, using three elastomeric members 512 placed in a spaced apart relationship along the longitudinal axis of the steerable sheath shaft 518 curve would indication direction of the sheath shaft 518 to a user. For example, elastomeric members 512 may be placed at the commencement of the sheath shaft curve 534, in the middle of the sheath shaft curve 532, and at the distal tip 530 of the sheath shaft 518 as best seen in FIGS. 20-21. Alternatively, as seen in FIG. 20, the most proximal elastomeric member 512 may be conical-shaped. This would indicate to a user which one of the elastomeric members is most proximal on the MR image. Otherwise, the user is viewing the image of three circles and would not be able to discern which direction the steerable sheath 100' is moving, i.e. distally or proximally. Alternatively, the elastomeric members 512 may increase in size in the proximal direction or in the distal direction. Elastomeric members of different sizes or shapes may indicate, as mentioned above, sheath and curve direction on the MR image. In the various multiple elastomeric member designs in accordance with the invention, a single lumen may be utilized for all three elastomeric members, or, alternatively, each elastomeric member may have its own separate lumen.

Figure 22:
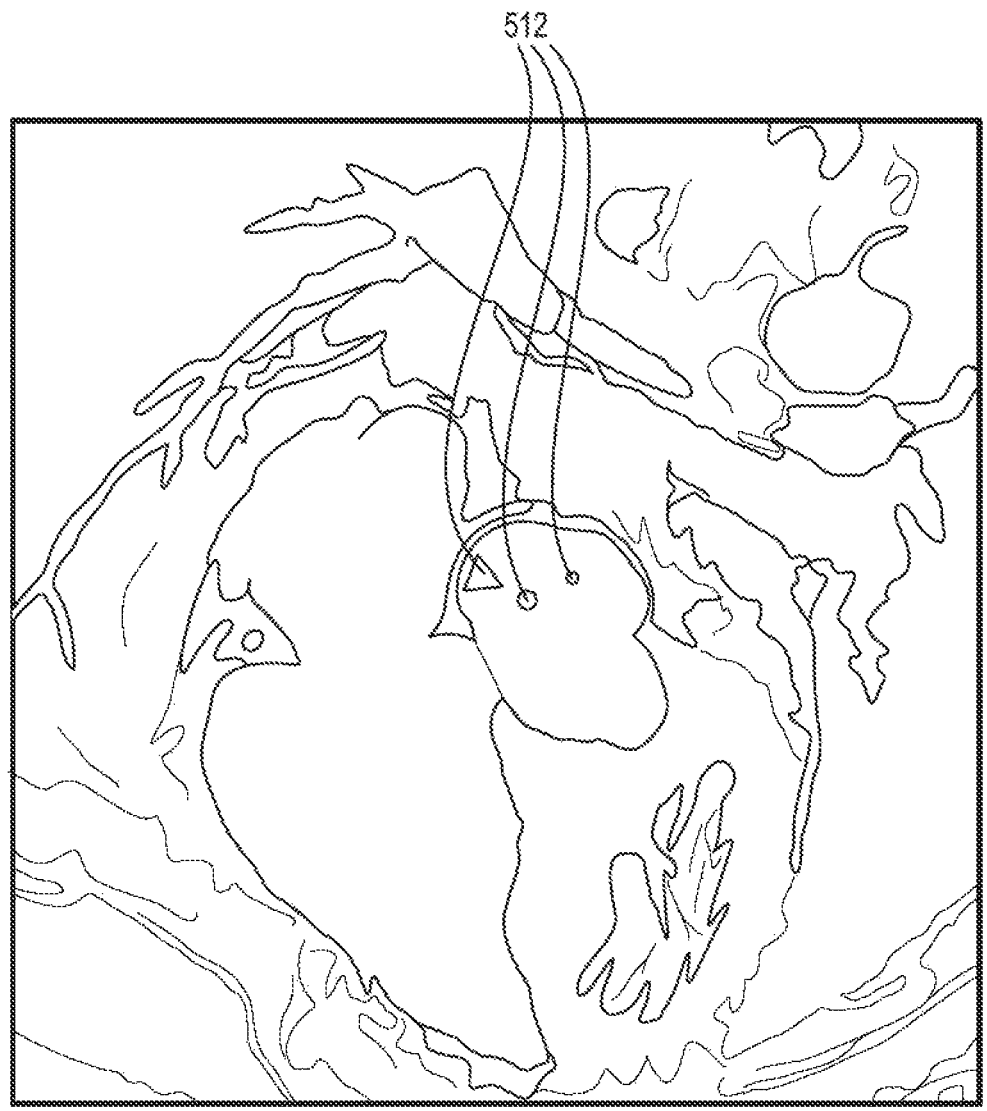
FIG. 22 is an MR image of the heart showing the curve shapes and direction of different elastomeric members.

Referring now to FIG. 22, an MR image of the heart is shown with a steerable sheath having multiple elastomeric members 512, 512, 512. The curve of the deflectable sheath may be seen as the most distal elastomeric member is deflected slightly toward the left. In this aspect of the invention, the most proximal elastomeric member 512 may be coned-shaped to indicate to a user the proximal portion of the steerable sheath.

Figure 23:
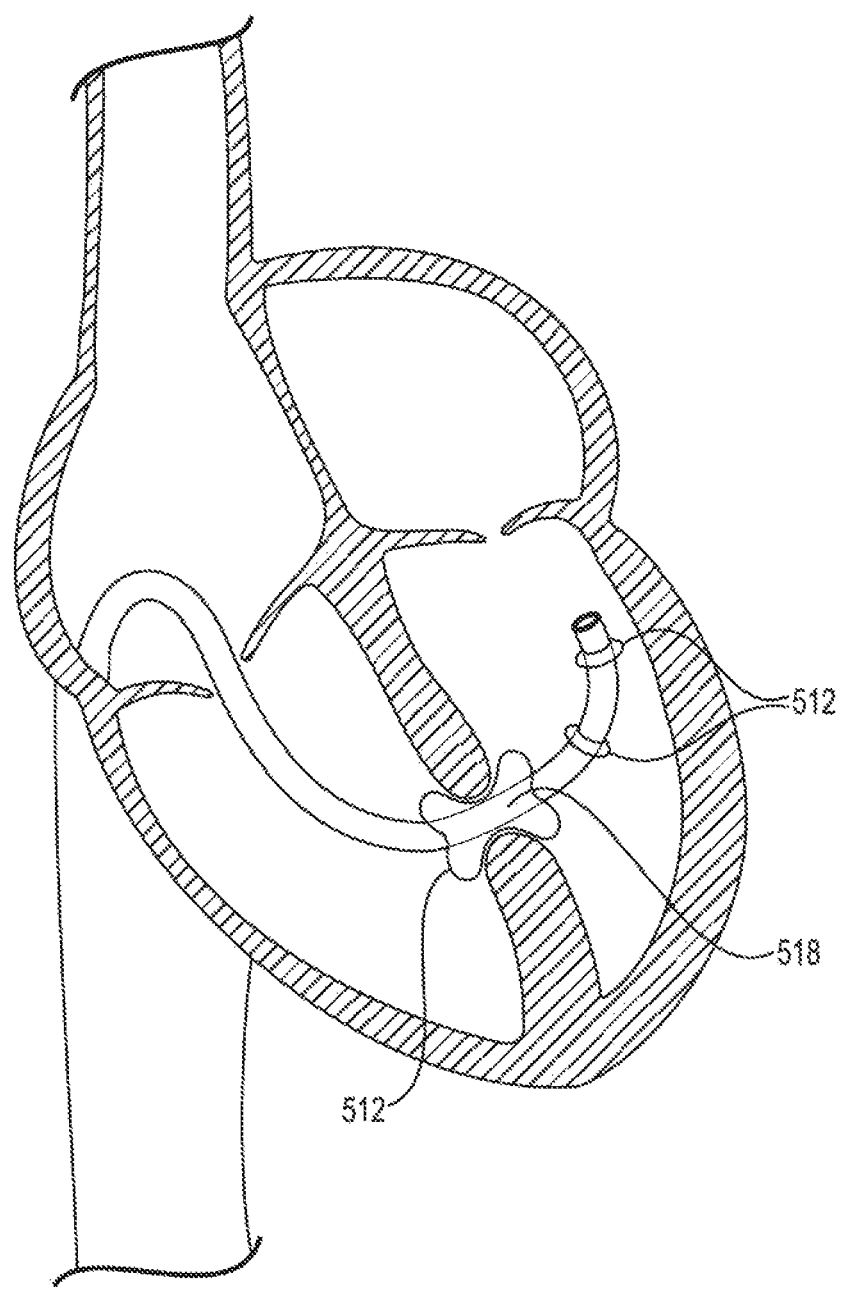
FIG. 23 is an illustration of the heart showing a most proximal dog bone-shaped elastomeric member that is utilized to anchor the shaft of the sheath in the atrial or ventricular septum.

FIG. 23 is an illustration of the heart showing a most proximal dog bone-shaped elastomeric member that is utilized to anchor the shaft of the sheath in the atrial or ventricular septum.

Although the present invention has been described with reference to various aspects of the invention, those of ordinary skill in the art will recognize that changes may be made in form and detail without departing from the spirit and scope of the invention.

We claim:

1. An MR compatible steerable sheath comprising:
a tubular shaft defining a longitudinal axis, said tubular shaft receiving first and second longitudinal movement wires operably coupled to a distal end thereof;
a control handle having a main body configured to receive first and second rack screws, said first and second rack screws being mechanically led to each other such that movement of said second rack screw along the longitudinal axis of the tubular shaft causes movement of said first rack screw in an opposite direction along the longitudinal axis of the tubular shaft, said second rack screw including a threaded portion on an outer surface at an end thereof; said first longitudinal movement wire operably coupled to said first rack screw and said second longitudinal movement wire operably coupled to said second rack screw; and a rotatable adjustment knob operably engageable with said control handle said rotatable adjustment knob having an internal threaded portion matingly engageable solely with the threaded portion of said second rack screw, said rotatable adjustment knob solely rotatably moveable between a first position and a second position in which the internal thread is configured to engage solely the thread on the outer surface of said second rack screw, wherein said first position causes said second rack screw to move proximally along the longitudinal axis of the tubular shaft which in turn causes said first rack screw to move distally along the longitudinal axis of the tubular shaft and proximal movement of said second rack screw is configured to tension and cause proximal longitudinal movement of the second longitudinal movement wire, and further wherein said second position is configured to move said second rack screw distally along the longitudinal axis of the tubular shaft which in turn causes said first rack screw to move proximally and distal movement of said second rack screw is configured to release tension on the second longitudinal movement wire;
an elastomeric member circumferentially positioned on said tubular shaft and including an elastomeric member lumen therewith;
a source of contrast media in fluid communication with said elastomeric member lumen,
wherein said elastomeric member is configured to denote the position of the steerable sheath.

2. The MR compatible steerable sheath of claim 1 wherein said elastomeric member lumen is in fluid communication with at least one tube defining a tube lumen configured to extend along a longitudinal axis of the tubular shaft on the outside of said tubular shaft.

3. The MR compatible steerable sheath of claim 1 wherein said elastomeric member comprises a plurality of elastomeric members each having an elastomeric member lumen.

4. The MR compatible steerable sheath of claim 3 wherein said plurality of elastomeric member lumens are each in fluid communication with a single tube lumen positioned on an outside of said tubular shaft.

5. The MR compatible steerable sheath of claim 3 wherein each of said elastomeric member lumens are in fluid communication with a plurality of tube lumens positioned on an outside of said tubular shaft.

6. The MR compatible steerable sheath of claim 3 wherein said elastomeric members are offset from each other along the longitudinal axis of said sheath.

7. The MR compatible steerable sheath of claim 6 wherein said elastomeric member and said sheath portion are constructed from the same material.

8. The MR compatible steerable sheath claim 1 wherein said elastomeric member includes a sheath portion operably coupled to said tubular shaft, said sheath portion defining a lumen therewithin in fluid communication with the lumen of said elastomeric member.

9. The MR compatible steerable sheath of claim 8 wherein said elastomeric member is integrally formed with said sheath portion.

10. The MR compatible steerable sheath of claim 9 wherein said elastomeric member and said sheath portion are constructed from different materials.

11. The MR compatible steerable sheath of claim 1 wherein said lumen is configured to allow the elastomeric member to be filled with viscous fluids.

12. The MR compatible steerable sheath of claim 1 wherein said elastomeric member has a shape selected from spherical, conical, dog-bone, tapered, circular, elliptical, cone-shaped and paddle-shaped.

13. The MR compatible steerable sheath of claim 1 wherein said elastomeric member comprises three elastomeric members positioned on said sheath in a spaced-apart relationship.

14. The MR compatible steerable sheath of claim 13 wherein each of said elastomeric members have a different shape configured to indicate to a user the direction of the steerable sheath when in use.

15. The MR compatible steerable sheath of claim 13 wherein one of said elastomeric members positioned proximal to the other elastomeric members has a shape different than said other elastomeric members.

16. The MR compatible steerable sheath of claim 1 wherein said elastomeric member is non-integrally formed with said sheath portion.

* * * * *